(12) United States Patent
Egawa

(10) Patent No.: US 8,128,795 B2
(45) Date of Patent: Mar. 6, 2012

(54) BIOSENSOR

(75) Inventor: Shunji Egawa, Nishitokyo (JP)

(73) Assignee: Citizen Holdings Co., Ltd., Tokyo (JP)

( * ) Notice: Subject to any disclaimer, the term of this patent is extended or adjusted under 35 U.S.C. 154(b) by 1236 days.

(21) Appl. No.: 11/390,476

(22) Filed: Mar. 28, 2006

(65) Prior Publication Data

US 2006/0243590 A1    Nov. 2, 2006

(30) Foreign Application Priority Data

Mar. 29, 2005  (JP) ................................. 2005-094089
Mar. 9, 2006  (JP) ................................. 2006-063791

(51) Int. Cl.
   *G01N 27/327* (2006.01)
(52) U.S. Cl. ................. 204/403.01; 422/506; 422/504
(58) Field of Classification Search ............ 204/403.01–403.15, 412; 422/506, 422/504, 533, 72; 137/625.4, 833
   See application file for complete search history.

(56) References Cited

U.S. PATENT DOCUMENTS

| | | | | |
|---|---|---|---|---|
| 4,618,476 A | * | 10/1986 | Columbus | ..................... 422/100 |
| 5,352,352 A | * | 10/1994 | Tsukada et al. | ............... 204/415 |
| 5,726,026 A | * | 3/1998 | Wilding et al. | ............... 435/7.21 |
| 6,299,757 B1 | * | 10/2001 | Feldman et al. | ............... 205/775 |
| 6,319,469 B1 | * | 11/2001 | Mian et al. | ........................ 422/64 |
| 6,582,662 B1 | * | 6/2003 | Kellogg et al. | ................. 422/72 |
| 2002/0175079 A1 | * | 11/2002 | Christel et al. | ................ 204/601 |
| 2004/0121450 A1 | * | 6/2004 | Pugia et al. | ................ 435/287.1 |
| 2005/0041525 A1 | * | 2/2005 | Pugia et al. | .................... 366/341 |

FOREIGN PATENT DOCUMENTS

JP   2002-310973 A    10/2002
JP   2004-109082 A    4/2004

* cited by examiner

*Primary Examiner* — Alex Noguerola
*Assistant Examiner* — Gurpreet Kaur
(74) *Attorney, Agent, or Firm* — Westerman, Hattori, Daniels & Adrian, LLP

(57) ABSTRACT

The present invention is directed to a biosensor being provided with a suction cavity which sucks a certain amount of sample by means of capillary phenomenon, the biosensor including a flow channel to connect the suction cavity and an analytical cavity furnished with a reagent, wherein, the flow channel has a narrowed section provided with a gap formed by narrowing a flow passage area. The narrowed section has a function to retain the sample in the suction cavity when the sample is sucked therein, and a function to circulate the sample retained in the suction cavity into the analytical cavity through the gap, when a centrifugal force is applied from the outside. The two functions held by the narrowed section enables a simple collection of blood sample, and further enables a simple transfer of the blood sample to the analytical area by applying the centrifugal force to the blood sample, as well as facilitating a component extraction.

19 Claims, 18 Drawing Sheets

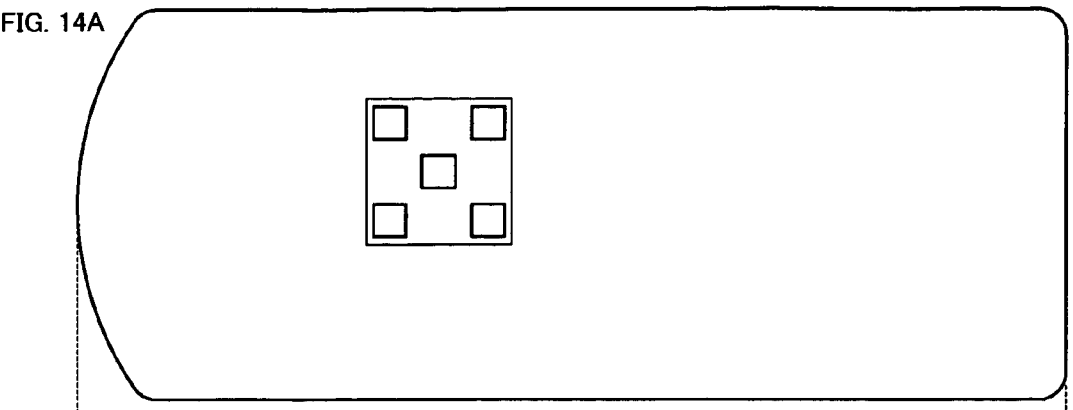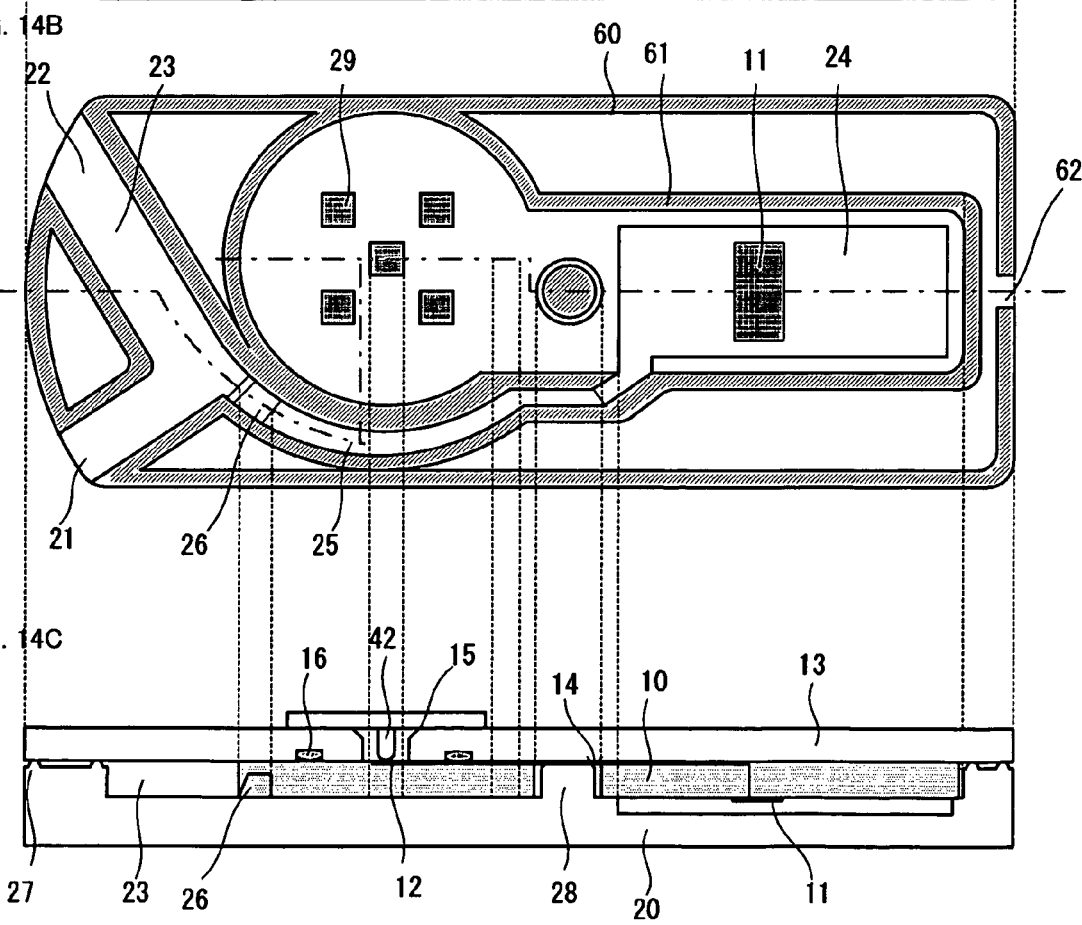

BIOSENSOR

DETAILED DESCRIPTION

1. Field of the Invention

The present invention relates to a biosensor having a structure for collecting a sample, and for transferring the sample thus collected to an analytical part.

2. Related Art

In recent years, due to a change in lifestyles, the number of patients with high-blood pressure, diabetes, and/or hyperlipemia is on the increase. These diseases are called as lifestyle-related diseases, and those may act as risk factors of arteriosclerosis. National and local governments are aiming at reducing mortality rate of stroke, that of ischemic heart disease, and of total cardiovascular disease, by modifying lifestyles.

Daily life control is an important approach for treating the lifestyle-related disease, and medical workers such as doctor, nurse, and pharmacist provide various advices on treatment.

In practice, however, due to busyness and negligence in daily life, a patient often fails to sufficiently control his or her own life for oneself. Even if it is found that the patient has any of these diseases in a physical examination, he or she neglects to have treatments due to the reason that there is no noticeable symptom. Therefore, in many cases, the condition is getting worse. Furthermore, it is extremely difficult and may be impossible for a medical worker to check whether or not the patient actually carries out the advised details in his or her daily life.

Considering the background as described above, it is required that the patient continuously executes, with one's strong will, a drug therapy, dietary therapy, and/or exercise therapy. Therefore, it is expected that the patient is made to be aware of his or her clinical condition on one's own at home, in addition to examinations conducted in a medical institution, for the sake of effective health control by the patient. It is because, if the patient conducts the examination for oneself, and reconsiders points to be improved in one's life style and future issues, based on the result of the examination, and further, if he or she feels fulfilled when a target of the treatment is achieved, self-supervised actions will be strongly supported.

In addition, it is also expected that this self-supervision may lead to maintenance and enhancement of motivation for treatment, and yield large benefits towards the treatment and prevention of the lifestyle-related disease. Given the situation above, testing equipment for home use is being well developed, so that the patient is allowed to take a test for oneself at home.

With a blood test in the field of clinical diagnosis, a disease state and/or a recovery state by treatment of a subject are grasped, by analyzing a particular component of the blood that has been collected. In this blood test, it is general that the collected blood is separated by component, and only a sample containing the element to be analyzed is subjected to the analysis. In many cases, a serum component is used as a target item for examination in a biochemical blood test.

As a representative example of testing equipment used for examination at home, SMBG (Self Monitoring of Blood Glucose) device has been developed which measures glucose concentration in blood (blood glucose level). In the examination employing the SMBG device broadly used these days, the subject oneself stabs a fingertip or an arm with puncture needle, and a small amount of blood sample having bled is utilized.

To be exact, the blood glucose level indicates glucose concentrations in the serum. The most common method for measuring the glucose concentrations is the one which utilizes an enzyme electrode. In this measuring method, a whole blood sample being collected is fed into a biosensor, and it is subjected to a measurement. The biosensor has an enzyme reaction layer inside. According to an amperometric measuring method, the enzyme reaction layer measures a current in accordance with the glucose concentration in the serum without hemolyzing the erythrocyte. In this measuring method, the concentration of a particular component in the serum is measured without separating the erythrocyte component.

A method which allows a patient to collect blood at home for oneself is limited to a particular method such as obtaining an extremely small amount of blood by stabbing a fingertip or an arm with puncture needle, as is the case using the SMBG device. The amount of blood obtained by this method is equal to or less than 50 microliter, in general.

Japanese Patent Laid-open Publication No. 2002-310973, pages 6 to 8, hereinafter, referred to as "Patent Document 1", discloses an electrochemical biosensor as a simple instrument for measuring blood glucose level, which measures the glucose concentration in the whole blood sample collected from human. This biosensor is provided with a suction port for sucking a sample, and when the whole blood sample as a test sample is provided to this suction port, the whole blood sample is sucked into a suction cavity called as a capillary fill chamber, by means of capillary phenomenon. This sucking into the suction cavity is performed by letting the air in the suction cavity out of a vent hole which is formed in the recesses of the suction cavity.

A working electrode and a counter electrode are arranged in this suction cavity. These electrodes obtain a measured current value being correlated with the glucose concentration, in a condition that the whole blood sample includes an erythrocyte component. Based on this measured current value, the blood glucose level can be measured easily.

Japanese Patent Laid-open Publication No. 2004-109082, pages 6 to 9, hereinafter, referred to as "Patent Document 2", discloses a biosensor for blood analysis which performs a plasma skimming by centrifugal operation. A flow channel of the biosensor for blood analysis is provided with a portion where an erythrocyte component is accumulated in the centrifugal direction upon centrifugal separation. With the centrifugal separation, the erythrocyte component is accumulated on the bottom, and a plasma component is separated as supernatant. In order to introduce the whole blood sample obtained from the subject as a sample, this biosensor is provided with an external pump at an outlet port, and the whole blood sample is suctioned by the suction negative pressure from the blood suction port. Similarly, it is also configured such that the plasma component after the centrifugal separation is transferred to an analytical position by the suction negative pressure from the external pump.

The biosensor as shown in the Patent Document 1 measures the glucose concentration in blood with a simple structure. This biosensor analyzes the whole blood in a condition that it includes the erythrocyte component without extracting plasma or serum component, and obtains a measured current value being sufficiently correlated with the glucose concentration in the serum.

However, when an examination item other than the glucose is analyzed, it is necessary in general to separate an erythrocyte component to extract only plasma or serum component, before the analysis is performed. If the examination is performed for the whole blood containing the erythrocyte component, the erythrocyte component is hemolyzed and mixed with the plasma component. Therefore, there has been a problem that concentration measurement cannot be performed accurately.

In addition, there is also a problem that if the biosensor has a structure that sucks the sample into the suction cavity via the capillary phenomenon from the suction port to the air vent, and the centrifugal operation is forced to be performed on this biosensor, the blood sample may spatter from the suction port or the air vent.

The Patent Document 2 discloses a structure of the biosensor adapted for the centrifugal separation. For this biosensor, however, it is necessary to install an external pump to generate a negative pressure for suction, to be prepared for the operation to feed the whole blood as a sample into the biosensor and for the operation to feed the plasma or serum component to the analytical position after the centrifugal separation. Therefore, there is a problem that peripheral equipment is grown in size and not suitable for at-home use equipment.

In order to extend the range of examination items for blood test available at home, not limited to the blood glucose level, a simple technique to extract plasma or serum component is required. However, in the conventional arts as described above, there is a problem that it is difficult to perform the blood component analysis with a simple structure.

An object of the present invention is to solve the above problem so as to achieve a blood component analysis with a simple structure.

SUMMARY OF THE INVENTION

A biosensor according to the present invention is provided with a suction cavity which sucks a certain amount of sample by means of capillary phenomenon, the biosensor including a flow channel to connect the suction cavity and an analytical cavity furnished with a reagent, wherein the flow channel has a narrowed section provided with a gap formed by narrowing a flow passage area. The narrowed section in the flow channel in the biosensor according to the present invention has a function to retain the sample in the suction cavity when the sample is sucked therein, and a function to allow the sample accumulated in the suction cavity to circulate into the analytical cavity through the gap, when a centrifugal force is applied from the outside while the sample is in a state of held in the suction cavity.

The biosensor of the present invention enables a simple collection of a blood sample according to the two functions provided by the narrowed section as described above. Further, with the centrifugal force against thus collected blood sample, transfer thereof to the analytical area can be performed in a simple manner, and in addition, a component extraction can be performed easily. The biosensor according to the present invention transfers the sample sucked into the suction cavity to the analytical cavity through the narrowed section provided in the flow channel, and at the time of centrifugal operation, it is possible to move the whole sample sucked in the suction cavity to the analytical cavity, thereby preventing a decrease of sample as a target for analysis, as well as preventing an external contamination due to spattering of the sample to the outside.

It is preferable that the analytical cavity of the biosensor according to the present invention is provided with an enzyme reaction layer for use in electrochemical measurement. With the amperometric measuring method, a current in accordance with the glucose concentration in serum can be measured without hemolyzing the erythrocyte by the enzyme reaction layer. Therefore, the concentration of a particular component in serum can be measured without separating the erythrocyte component.

Furthermore, in the analytical cavity of the biosensor according to the present invention, a plurality of enzyme reaction layers are separately arranged along a direction to which the centrifugal force is applied, and components of the sample being separated can be measured.

The suction cavity of the biosensor according to the present invention is provided with two openings placed in parallel, perpendicularly to the direction to which the centrifugal force is applied, and a jointed portion which establishes connection with the flow channel. At the jointed portion, a line from each of the openings to this jointed portion crosses the direction to which the centrifugal force is applied, in a positional relationship to form an obtuse angle. It is also assumed that this obtuse angle is any arbitrary angle at least 90 degrees.

Here, one of the openings acts as a suction port to suck the sample into the suction cavity, and the other opening acts as an outlet port which discharges the air existing in the suction cavity when the sample is sucked into the suction cavity.

According to the arrangement of the suction cavity as described above, the sample existing in the suction cavity receives a force directing to the flow channel from the suction cavity, the force being caused by a centrifugal force, whereby the sample is allowed to be introduced into the flow channel. With the positional relationship of the two openings and the angular relationship at the jointed portion as described above, when the centrifugal force is applied to the sample that is retained within the suction cavity, it is possible to keep the sample not to go out of any of the openings, and then introduce the sample into the flow channel.

It may also be possible to furnish a reagent in the suction cavity, for pretreating the sample above.

In the biosensor according to the present invention, the suction cavity, the flow channel, and the analytical cavity are formed by bonding two plate-like members with surfaces opposed to each other, one or both the surfaces having concave-convex parts. In addition, the biosensor may be configured such that an electrode substrate is placed between the two plate-like members, and an electrode provided on this electrode substrate is exposed in the analytical cavity. This electrode detects a measured current in accordance with the component concentration of the sample that is introduced in the analytical cavity.

At least one of the plate-like members is provided with a window part which electrically connects a connector intended for external connection with an external circuit, the connector being electrically connected with the electrode on the electrode substrate. Therefore, through this window part, the external circuit is allowed to be electrically connected with the connector, and it is possible to derive to the external circuit, the measured current detected by the electrode within the analytical cavity.

The plate-like member may be provided with a leak prevention member, such as an O-ring or a packaging member, which surrounds the window part. Even when the sample leaks from the analytical cavity, the leak prevention member can prevent the connector intended for external connection within the window part, from coming into contact with the sample. This leak prevention member may have a configuration to surround each of the multiple window parts independently, instead of surrounding the multiple parts as a whole.

In addition, the connector intended for external connection is placed at a position closer to the center of the centrifugal force, which is at least closer than the analytical cavity, in the direction to which the centrifugal force is applied. With this arrangement, at the time of applying the centrifugal force, the sample within the analytical cavity receives a force in the direction being apart from the connector, due to the centrifugal force, and thus it is possible to avoid contact between the connector and the sample.

The biosensor according to the present invention applies ultrasonic welding to the outer circumferential part of the suction cavity, the flow channel, and the analytical cavity. With this ultrasonic welding, it is possible to prevent the sample introduced into the biosensor from leaking to the outside. In addition, the outermost circumferential part of the plate-like member may also be subjected to the ultrasonic welding.

It is further possible to configure the biosensor according to the present invention such that hydrophilic coating is applied on a wall surface of the suction cavity, thereby facilitating suction of the sample from the outside into the suction cavity. This hydrophilic coating can be formed by applying surfactant.

In addition, it is possible to configure the narrowed section as hydrophobic, the narrowed section being provided in the flow channel of the biosensor according to the present invention. With this configuration, it is possible to prevent the sucked sample from being introduced into the flow channel without stopping, when the sample is sucked in the suction cavity in the condition where no centrifugal force is applied. Accordingly, a certain amount of the sample can be sucked into the suction cavity. In addition, hydrophobicity of this narrowed section can be obtained by forming the narrowed section with a hydrophobic synthetic resin. Alternatively, the hydrophobicity of the narrowed section may be formed by applying water-repellent treatment thereon.

The narrowed section included in the biosensor according to the present invention may be configured, for example, to be provided with a first portion where the flow channel area is gradually decreased on the suction cavity side, and a second portion where the flow channel area stays narrow for a predetermined distance between the suction cavity side and the flow channel side, and the narrowed section has a shape that the flow channel area changes in the rear of the second portion, from the area being narrowed to the original area of the flow channel. With this configuration above, it is possible to retain the sample within the suction cavity when the sample is sucked therein, and when a centrifugal force is applied from the outside, the sample accumulated in the suction cavity is allowed to circulate into the analytical cavity through the gap.

The biosensor sucks up the blood sample into the suction cavity from the suction port by capillary phenomenon. The biosensor which has sucked up the blood sample in the suction cavity is installed on a turntable. The turntable rotates the biosensor to apply a centrifugal force. In the biosensor given the centrifugal force, the whole blood sample retained in the suction cavity is fed into the analytical cavity passing through the narrowed section. The blood sample that received the centrifugal force is separated to the positions within the analytical cavity according to specific gravities. The positions to which the blood sample is separated are associated with the components of the blood sample. According to the separated positions, the components of the blood sample can be identified. Electrodes are arranged in such a manner as being associated with the separated positions respectively, whereby concentration of each component of the blood sample can be measured, based on the measured current on each electrode.

The biosensor according to the present invention sucks a small amount of blood sample having bled, by stabbing a fingertip or an arm with puncture needle. Thereafter, a centrifugal force is applied to the biosensor, and then the sample blood is transferred to the analytical cavity. Further, the blood sample is separated by component through the centrifugal separation. Out of the components thus separated, a component containing a substance to be analyzed is subjected to analysis.

With the configuration above, a biosensor adaptable for a blood test which requires extraction of plasma or serum component can be provided.

The biosensor according to the present invention has a simple structure in which an analyzer only applies a centrifugal force, and any large-scale peripheral equipment such as an external pump is not necessary. Therefore, this structure is suitable for at-home use equipment.

In the biosensor according to the present invention, only one rotating motor enables two actions, i.e., transfer of the blood sample to the analytical position and separation of the blood by component, and thus extremely simple mechanism has been achieved.

DESCRIPTION OF THE DRAWINGS

FIG. 14A, FIG. 14B, and FIG. 14C are explanatory views to explain the biosensor according to the third embodiment of the present invention.

DETAILED DESCRIPTION

Figure 2:
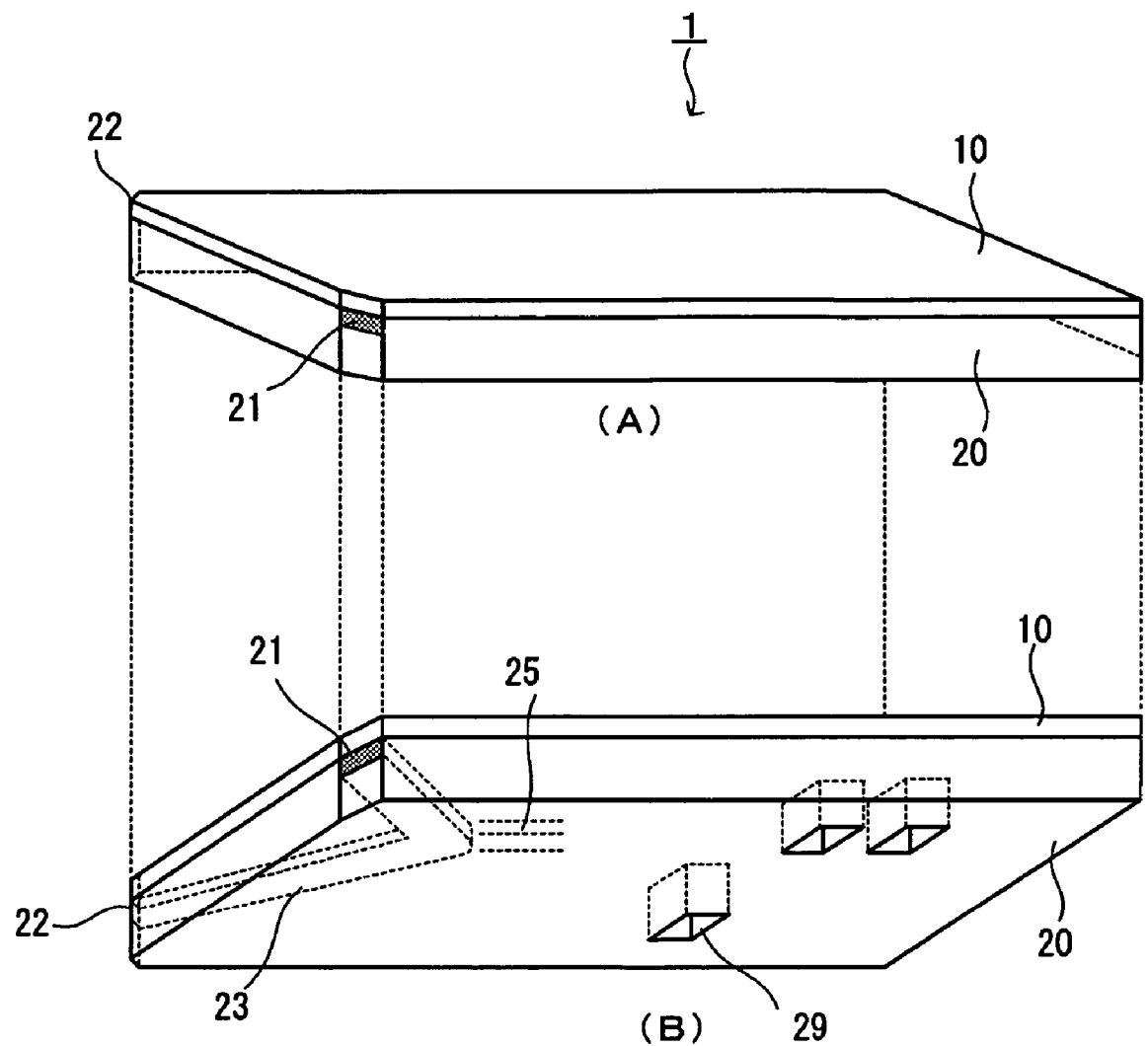
FIG. 2A and FIG. 2B are external views of the biosensor according to the present invention, viewed from the obliquely upward and downward directions respectively.

Initially, the first embodiment of a biosensor according to the present invention will be explained. FIGS. 2A and 2B are external views each showing one embodiment of the biosensor according to the present invention. The biosensor 1 has a structure that a lower plate 20 and an electrode substrate 10 are bonded together. FIG. 2A is an illustration of the biosensor viewed from the electrode substrate 10 side, and FIG. 2B is an illustration of the biosensor viewed from the lower plate 20 side.

A suction port 21 is provided on one side surface of the biosensor 1, and an air vent 22 is provided on the other side surface. There is provided a cavity from the suction port 21 to the air vent 22, the cavity being formed by a portion sandwiched between the lower plate 20 and the electrode substrate 10. This cavity is a suction cavity 23, which is a space to suck a sample such as a certain amount of blood and to retain the sample temporarily. This biosensor is configured such that blood as a sample is sucked from the suction port 21 by capillary phenomenon, and the air inside the suction cavity 23 is discharged from the air vent 22. After the suction is finished, the suction cavity 23 is filled with blood. It is to be noted here that either of those openings may be defined as the suction port or the air vent 22 arbitrarily and the opening of reference numeral 21 may be defined as the air vent, and the opening of reference numeral 22 may be defined as the suction port.

A part of the suction cavity connecting to the suction port 21, and a part of the suction cavity connecting to the air vent 22 are joined inside the biosensor 1, and the suction cavity is further connected to a flow channel 25 which is directed to an analytical cavity (not illustrated in FIG. 2A and FIG. 2B).

There is a connector window 29 on the backside of the biosensor 1. Here, it is assumed that the electrode substrate 10 side is defined as a front side, and the lower plate 20 side is defined as a backside, but the front and back sides are defined as such for descriptive purposes. Therefore, the front-back side relationship may be defined the other way around.

In FIG. 2B, a connector terminal 12 (not illustrated) is placed in the recess of the connector window 29. This connector terminal 12 is a contact point terminal installed on the electrode substrate 10, and it is electrically connected by wiring to the electrode provided within the analytical cavity. The connector terminal 12 performs electrochemical measurement by electrically connected to an external analyzer.

The electrode substrate 10 which constitutes the substrate on which after-mentioned electrode is disposed, also serves as an upper plate as opposed to the lower plate 20.

Figure 1A:
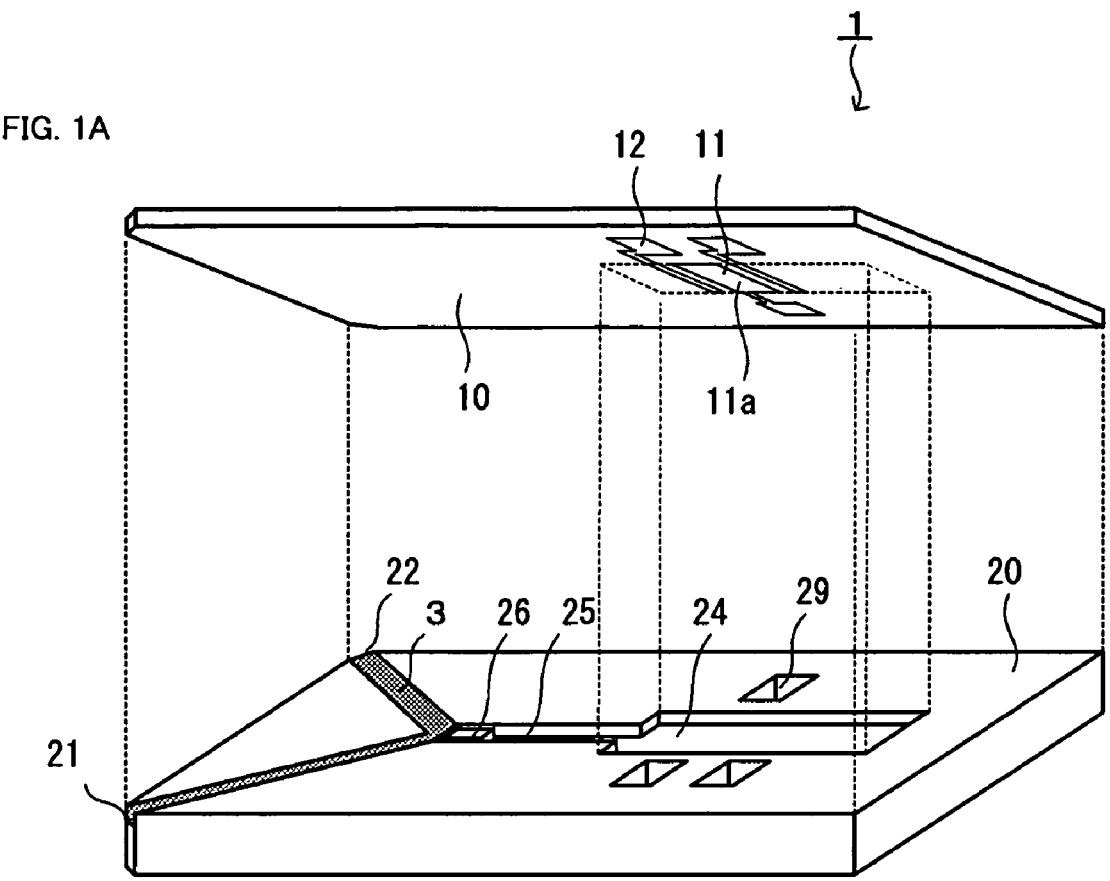
FIG. 1A and FIG. 1B are exploded perspective views showing a biosensor according to the present invention.
Figure 1B:
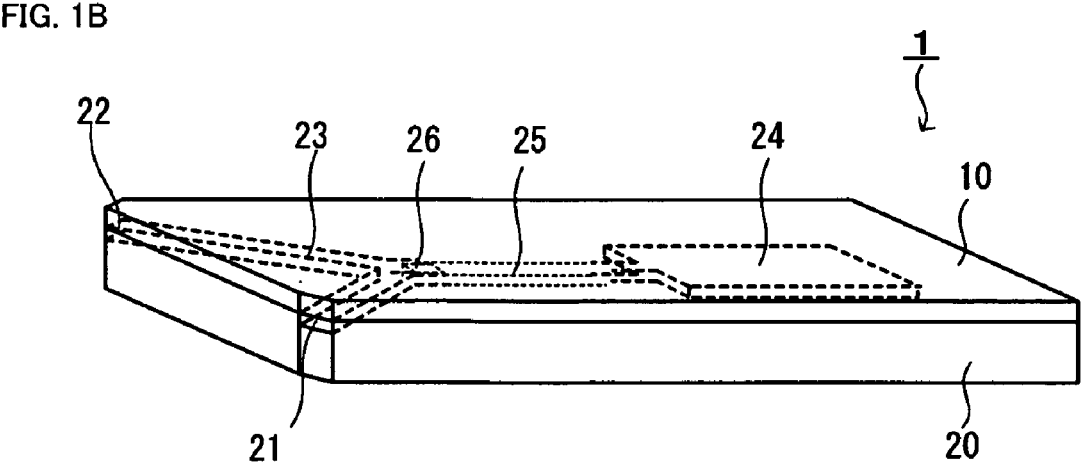

FIG. 1A and FIG. 1B are exploded perspective views of the biosensor 1. The lower plate 20 is made of transparent plastic, and the suction cavity 23, analytical cavity 24, and flow channel 25 being a groove for carrying a sample are formed thereon. FIG. 1A shows a state where a certain amount of blood 3 is sucked into the suction cavity 23. On a part of the flow channel 25, there is provided a wall portion being joined to the flow channel, so as to form a narrowed section 26. When a certain amount of blood as a test sample is sucked into the suction cavity 23, the blood 3 is held back by the wall portion of the narrowed section 26, and retained in the suction cavity 23. This is because there is no structure of air vent in the flow channel 25, nor in the analytical cavity 24. The blood 3, in a state of being sucked into the suction cavity 23 simply by capillary phenomenon, may enter up to the midway of the wall portion of the narrowed section 26, but it may never flow into the flow channel 25 over the narrowed section 26. In order that the blood 3 moves into the flow channel 25 and further into the analytical cavity 24, an operation by the centrifugal force as described below is necessary.

The flow channel 25 is a groove connecting the suction cavity 23 with the analytical cavity 24. The narrowed section 26 is a part of the flow channel 25 on the position adjacent to the suction cavity 23, and it is provided with a narrow gap which allows the blood 3 within the suction cavity 23 to circulate into the analytical cavity 24 when the centrifugal force is applied. The analytical cavity 24 is a space in the groove formed on the lower plate 20, covered by the electrode substrate 10. The upper and lower surfaces of the analytical cavity 24 is covered respectively by the electrode substrate 10 and the lower plate 20, and the side surface is covered by the wall portion of the lower plate 20. The analytical cavity 24 has a structure that a part of side surface thereof has an opening connecting to the flow channel 25, and the blood 3 is flown from the flow channel 25 through this opening.

In addition, the analytical cavity 24 is furnished with a reagent to analyze the blood. When a centrifugal force of a certain strength or more is applied from the outside, the blood 3 goes over the wall portion of the narrowed section 26 which has been holding back the blood, and flows into the flow channel 25, and further it is fed into the analytical cavity 24 by way of the flow channel 25. At this timing, a part of the air existing in the analytical cavity 24 is let out of the analytical cavity 24, through the flow channel 25 and the suction cavity 23. Reaction occurs between the blood flown into the analytical cavity 24 and the reagent, and then the blood is analyzed.

Here, a positional and directional relationship of the suction cavity 23, the narrowed section 26, and the flow channel 25 will be explained. If it is assumed that the direction to which the centrifugal force is applied is at 6 o'clock position of analog clock, the suction port 21 as an inlet port for the blood sample is at 10 o'clock position, the air vent 22 as an outlet port for the air is at 2 o'clock position, and the flow channel 25 to feed the blood sample into the analytical cavity 24 is at 6 o'clock position. In other words, the two openings (suction port 21 and air vent 22) of the suction cavity 23 are placed side by side, perpendicularly to the direction to which the centrifugal force is applied, and at a jointed portion which establishes connection between the suction cavity 23 and the flow channel 25, the line connecting each opening and the joint crosses the direction to which the centrifugal force is applied, in a positional relationship to form an obtuse angle. According to a top view of the biosensor 1, the suction cavity 23, the flow channel 25, and the analytical cavity 24 form a Y-shape.

With the positional and directional relationship as described above, the sample within the suction cavity receives a force directing to the flow channel by the centrifugal force. When the centrifugal force is applied, the blood 3 retained in the suction cavity 23 all goes over the narrowed section 26, and it is fed into the analytical cavity 24 by way of the flow channel 25, without leaking from the suction port 21 and the air vent 22.

For the sake of convenience in the example above, the suction port 21 and the air vent 22 are explained separately, but these two inlet/outlet portions have the same shape. Therefore, they are applicable in reverse way, that is, the sample may be sucked from the inlet/outlet port at 2 o'clock position. It is explained that when the direction of centrifugal force is at 6 o'clock position, the openings are oriented to 2 o'clock position and 10 o'clock position respectively. However, as far as an obtuse angle is formed by the angular relationship at the jointed portion, the orientations of the openings are not limited to the above example.

One example of cross section of the suction cavity 23 has a dimension of around 1.5 mm in width×0.3 mm in depth, and a cross sectional area is 0.45 mm$^2$. It is desirable that the cross section of the gap in the narrowed section 26 is around 1 mm in width×0.1 mm in depth and the cross sectional area is 0.1 mm$^2$, which makes the gap extremely fine. It is also desirable to form the wall portion of the narrowed section 26 with the length of 3 mm, which is relatively long. The numerical values above are just examples, and the dimension of the narrowed section 26 is not limited to the above values, under the condition that the dimension allows the blood to be held in the suction cavity 23 until a predetermined centrifugal force is applied, and when the centrifugal force of the predetermined strength and more is applied, a resistance strong enough to flow the blood towards the flow channel side 25 is generated.

Furthermore, there is pierced a connector window 29 on the backside of the lower plate 20, so as to establish electrical connection with a connecter terminal 12 (not illustrated in FIG. 1A to FIG. 2B). The electrode substrate 10 is an FPC (flexible print circuit) made of polyester film of PET (polyethylene terephthalate), for example, and the connector terminal 12 is arranged on the surface above the connector window 29. An electrode 11 prepared for electrochemical measurement is arranged on the surface above the analytical cavity 24. This electrode 11 includes a working electrode, a counter electrode, and a reference electrode.

The working electrode of the electrode 11 is a carbon electrode, and on the surface thereof, there is formed an enzyme reaction layer. 11a including oxidoreductase being a reagent and electron-transfer mediator. The counter electrode and the reference electrode of the electrode 11 are silver-silver chloride electrode. For example, in the case of the biosensor which measures glucose, glucose oxidase is used as the oxidoreductase, and potassium ferricyanide is used as the electron-transfer mediator, respectively.

Figure 4A:
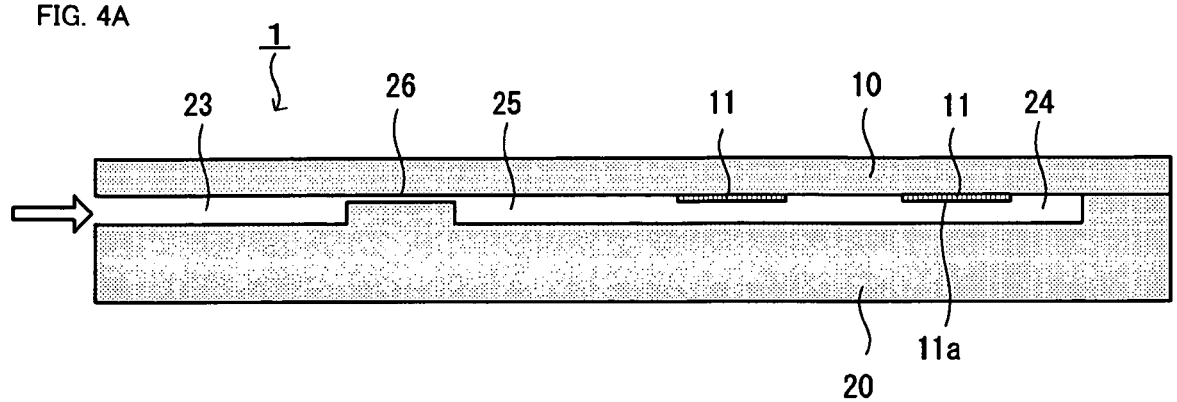
FIG. 4A, FIG. 4B, and FIG. 4C are cross sectional views showing the biosensor according to the present invention.
Figure 4B:
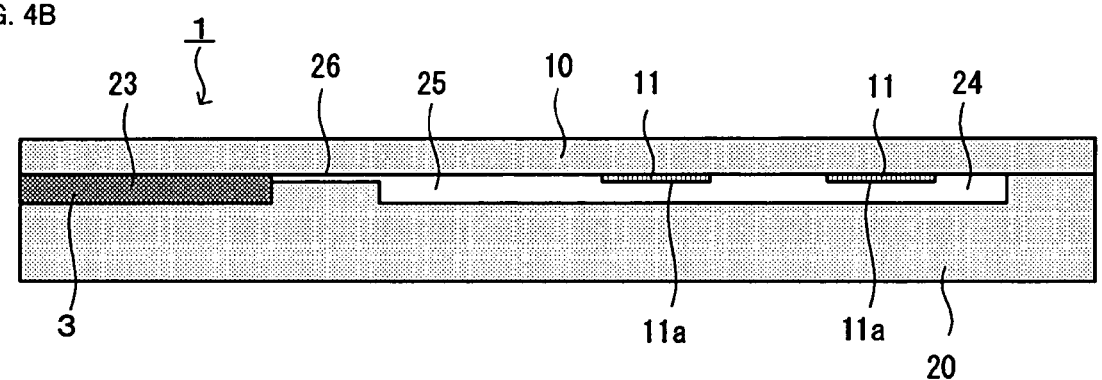
Figure 4C:
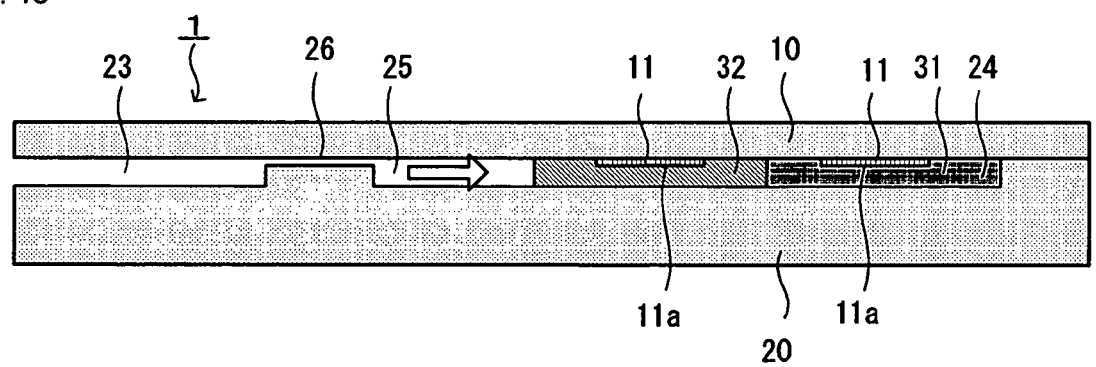

FIG. 4A to FIG. 4C are cross sectional views of the biosensor 1. FIG. 4A shows a state before the blood 3 is sucked, and FIG. 4B shows a state where the blood 3 has been sucked into the suction cavity 23. The narrowed section 26 is formed in a part of the flow channel 25 on the position adjacent to the suction cavity 23. When a certain amount of blood as a test sample is sucked into the suction cavity 23 simply by the capillary phenomenon without applying a centrifugal force, the blood 3 does not pass through the gap of the narrowed section 26, and it will flow into neither the flow channel 25 nor the analytical cavity 24. In other words, the blood 3 is held back by the cross wall 26, and retained in the suction cavity 23.

FIG. 4C shows a state in which the blood is centrifugally separated by blood component, into erythrocyte component 31 and plasma component 32. With the centrifugal force applied from the outside, the blood 3 being a sample accumulated in the suction cavity 23 passes through the gap in the narrowed section 26, and flows out toward the flow channel 25. Furthermore, the blood as a sample is fed into the analytical cavity 24 in which the enzyme reaction layer 11a furnished with a reagent is formed. The blood introduced into the analytical cavity 24 is centrifugally separated by component, into the erythrocyte component 31 and the plasma component 32, according to the centrifugal force applied from the outside. A plurality of enzyme reaction layers 11a are positioned along the direction of the centrifugal force, each enzyme reaction layer is made to be associated with the component of the sample having been subjected to the centrifugal separation.

Next, with reference to FIGS. 2A, 2B, and FIGS. 1A, 1B, operations of the biosensor 1 will be explained. Here, operations from the time when the blood is sucked, which has been obtained by puncture, until when the blood is analyzed by the analyzer 2 provided with a centrifugal facility.

Firstly, a fingertip as a blood collection area is pricked with puncture needle, and blood of at least a certain amount required for analysis is let out. The amount of blood required for analysis is around 10 μL, for example, and the capacity of the suction cavity 23 is the same as this required volume, in order to suck this necessary amount of blood. Then, the blood (whole blood) is brought into contact with the suction port 21 of the biosensor 1. The blood 3 is sucked by capillary phenomenon, and the suction cavity 23 from the suction port 21 to the air vent 22 is filled with the blood. It is possible to configure the suction cavity 23 such that the wall surface thereof is made to be hydrophilic by applying hydrophilic coating such as surfactant and the like, thereby facilitating sucking of the blood. Furthermore, it may also be configured such that membranes are arranged in the suction cavity.

At this timing, the blood 3 may enter up to the midway of the wall portion of the narrowed section 26, but it will never pass through the gap of the narrowed section 26 to flow into the flow channel 25 side. This is because resistance against the flow is raised by the gap formed in the narrowed section 26, and discharging of air to the downstream side is limited due to the narrowed section 26. The space formed by the flow channel 25 and the analytical cavity 24 is a closed space having no air vent that allows the internal air to go out. Due to the structure that the internal air existing in the flow channel 25 and the analytical cavity 24 is not let out, the blood 3 will not flow into the direction to the flow channel 25.

It is to be noted here that the blood 3 being sucked can be checked from the backside of the lower plate 20, which is made of transparent plastic. If the blood is not sucked enough to fill the suction cavity 23, the blood is again let out from the puncture area of the fingertip and it is additionally sucked from the suction port 21. The procedure above enables the suction cavity 23 to suck a certain amount of blood as a test sample.

Furthermore, in the analysis which requires a pretreatment reaction, a reagent is placed in the suction cavity, thereby carrying out the pretreatment targeting the whole blood in the state where the whole blood has been sucked. For example, if the pretreatment is protease treatment, protease as a reagent for this treatment is placed in advance in the suction cavity 23, whereby the plasma protein can be processed to amino acid by the protease treatment. This reagent is, for instance, applied on the inner wall of the suction cavity 23 and then dried. Alternatively, it may be provided on the membrane.

Figure 5:
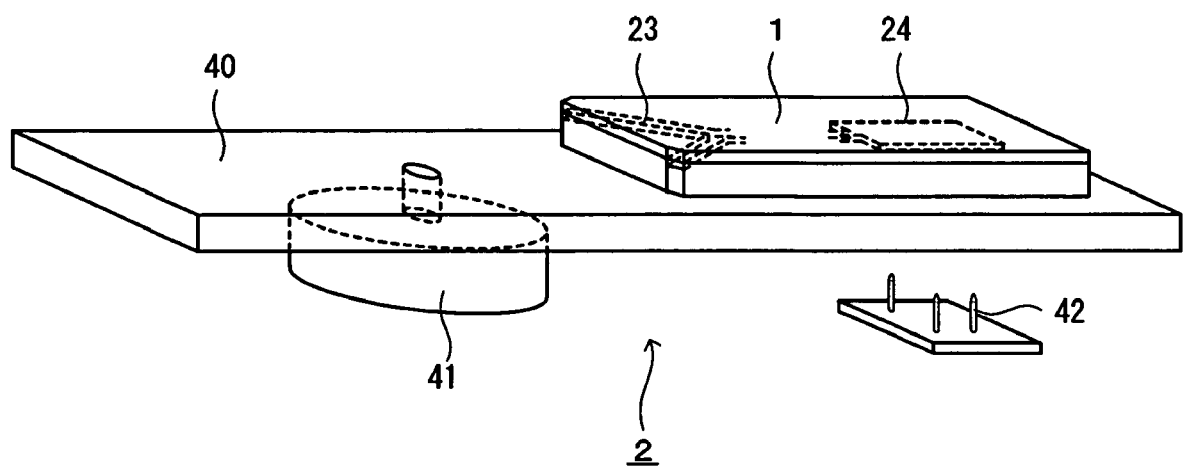
FIG. 5 is a schematic configuration diagram showing a centrifugal facility on which the biosensor according to the present invention is installed.

Next, with reference to FIG. 5, a structure of the analyzer 2 having the centrifugal facility, on which the biosensor 1 is mounted, will be briefly explained. It is to be noted here that FIG. 5 shows only a schematic structure of the centrifugal mechanism of the analyzer 2, and other elements such as electrochemical measuring part, display part, and operation switch part are omitted.

A turntable 40, motor 41, and spring connector 42 constitute the centrifugal facility part of the analyzer 2. The turntable 40 is a mounting table on which the biosensor 1 is mounted and which rotates at high speed. The motor 41 is a drive motor to rotate the turntable 40 and the biosensor 1, and it is, for example, a DC motor with a rotation velocity of 5,000 times per minute. The spring connector 42 electrically connects the connector terminal 12 of the biosensor 1 (not illustrated in FIG. 5) with the electrochemical measuring part in the analyzer. Here, when the biosensor 1 is set for analysis, it is mounted on the turntable 40 of the analyzer 2 with the centrifugal facility, in such a manner that the suction cavity 23 is positioned on the rotational center side, and the analytical cavity 24 is positioned on the rotational outer circumferential side. When an operation switch of the analyzer 2 is pressed, the turntable 40 starts rotation. The rotation speed gradually increases, and the highest rotation speed is, for example, 5,000 times per minutes, and this rotation continues for five minutes. Accordingly, a certain amount of centrifugal force is applied to the biosensor 1 from the external analyzer 2. If the turning radius from the rotation center to the edge of the analytical cavity 24 is 7 cm, the centrifugal force on the edge of the analytical cavity 24 is approximately 2,000 times larger than the gravity.

Figure 3:
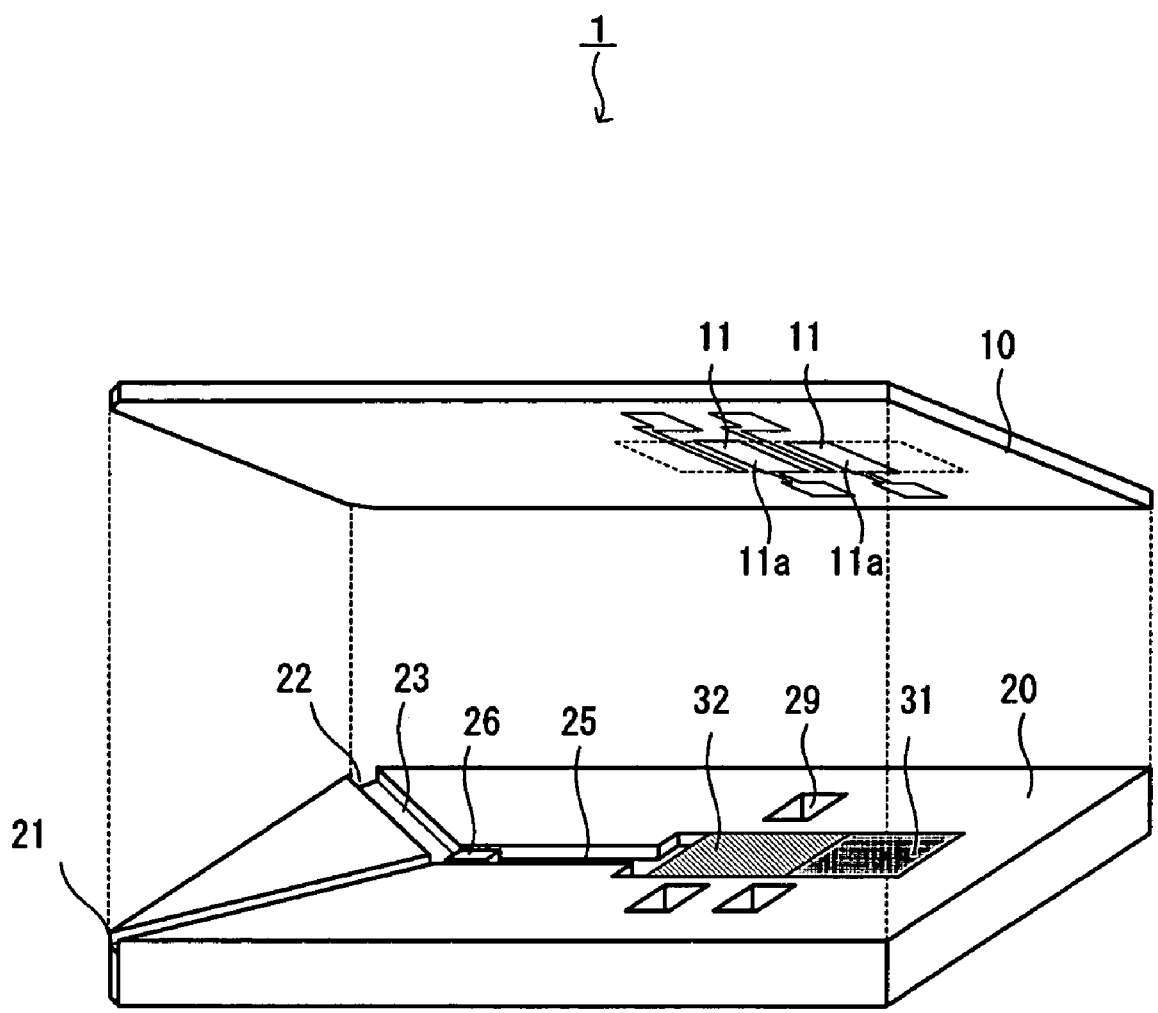
FIG. 3 is an exploded perspective view showing a state of being centrifuged in the biosensor according to the present invention.

FIG. 3 is an exploded perspective view showing a state where the biosensor has been subjected to the centrifugal separation. With reference to FIG. 3, transferring process of the blood 3 inside the biosensor 1 will be explained. At first, in a state where the blood 3 is collected and the centrifugal force has not been applied yet, the suction cavity 23 is filled with the blood 3 as shown in FIG. 1A. In this stage, the blood 3 is held back by the narrowed section 26.

Thereafter, as shown in FIG. 5, the turntable 40 on which the biosensor 1 is mounted is rotated. Then, the centrifugal force is applied to the biosensor in the centrifugal direction, in other words, towards the 6 o'clock position on analog clock. With the centrifugal force thus applied, all the blood 3 accumulated in the suction cavity 23 is allowed to pass through the gap in the narrowed section 26 located at 6 o'clock position, and to be fed into the analytical cavity 24 by way of the flow channel 25, without leaking from the suction port 21 and the air vent 22 placed at 10 o'clock position and 2 o'clock position, respectively.

Thereafter, the rotary motion of the turntable 40 continues, and with additional certain level of centrifugal force from the outside, the blood 3 starts separating centrifugally into the erythrocyte component 31 and to the plasma component 32, by specific gravity. For example, if the turntable is rotated at rotation speed of 5,000 times per minute for 5 minutes continuously, since the specific gravity of the plasma component 32 is relatively smaller than the erythrocyte component 31, the erythrocyte component 31 and the plasma component 32 are positioned in this order from the place where the turning radius is longer in the analytical cavity 24. The enzyme reaction layer 11a is placed at a position in the analytical cavity 24, where the plasma component 32 is extracted (see FIG. 4C).

Next, when the separation by component as to the erythrocyte component 31 and the plasma component 32 is finished, the turntable 40 on which the biosensor 1 is mounted stops rotating. Spring connector 42 of the analyzer 2 is connected to the connector terminal 12 of the biosensor 1 (not illustrated in FIG. 3). On the surface above the position of the analytical cavity 24 where the plasma component 32 is located, there is placed a working electrode of the enzyme reaction layer 11a furnished with a reagent for analysis. Accordingly, enzymatic reaction occurs in the enzyme reaction layer 11a placed in the analytical cavity 24, and it is possible to perform electrochemical measurement by the biosensor 1.

As described above, the biosensor 1 sucks a certain amount of blood into the suction cavity 23 by capillary phenomenon. Thereafter, when a centrifugal force is applied, the blood 3 is allowed to pass through the gap of the narrowed section 26 which has been holding back the blood 3, and it then is fed into the analytical cavity 24 in which a reagent is furnished. Additional centrifugal force is applied on this biosensor, and the plasma component 32 or serum component are extracted from the sample blood 3 by centrifugal separation. Accordingly, it is possible to analyze the blood component by a simple method.

Figure 6:
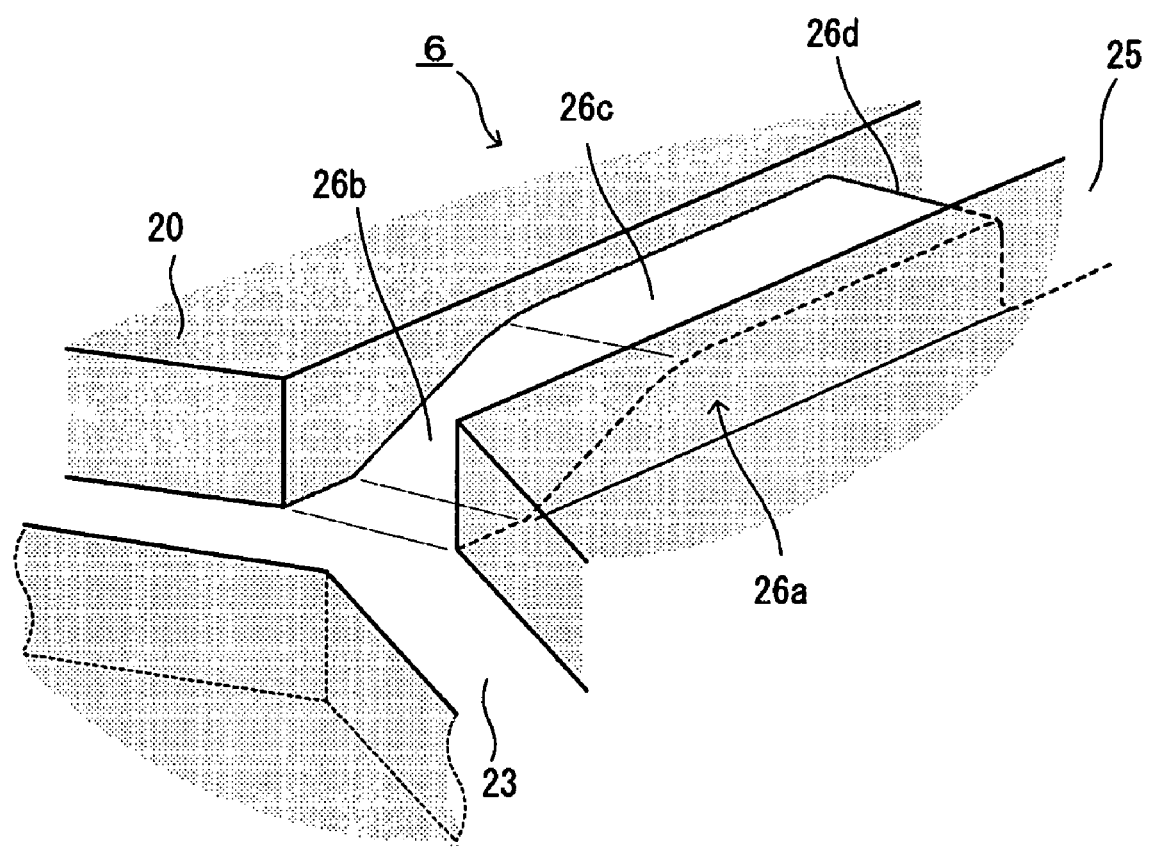
FIG. 6 is a perspective view showing the narrowed section provided in the biosensor according to the present invention.

Next, the narrowed section 26 provided in the biosensor according to the present invention will be explained with reference to FIG. 6, FIGS. 7A to 7D, FIGS. 8A to 8D, and FIG. 9. FIG. 6 and FIG. 9 each is a perspective view of the narrowed section, and FIGS. 7A to 7D and FIGS. 8A to 8D are cross sectional views of the narrowed section.

FIG. 6 shows one configuration example of the narrowed section, and FIGS. 7A to 7D show cross sections of this narrowed section. FIG. 6 shows a groove part formed on the lower plate 20 side, and an upper plate-like member such as electrode substrate 10 is omitted.

The narrowed section 26 as shown in FIG. 6 and FIGS. 7A to 7D has a structure that a wall part 26a is projected from the lower plate 20, thereby narrowing gap space between the lower plate 20 and the electrode substrate 10. The wall part 26a includes a first portion 26b whose flow channel area gradually decreases on the suction cavity 23 side and a second portion 26c which stays narrowing the flow channel area for a predetermined distance between the suction cavity 23 side and the flow channel 25 side, and on the downstream side of the second part 26c, it further includes a third portion 26d where the narrowed flow channel area increases to the original flow channel area. The shape of the cross section of the narrowed section 26 forms a gentle slope at the first portion 26b, and a flat surface at the second portion 26c for a predetermined distance, and at the third portion 26d, the second portion 26c is changed to the surface of the flow channel 25 (see FIG. 7A).

Figure 7A:
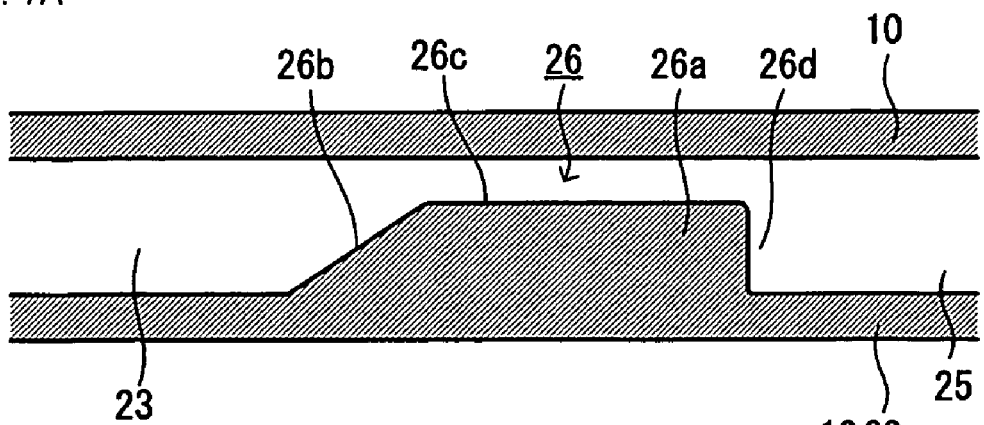
FIG. 7A, FIG. 7B, FIG. 7C, and FIG. 7D are cross sectional views showing the narrowed section provided in the biosensor according to the present invention.
Figure 7B:
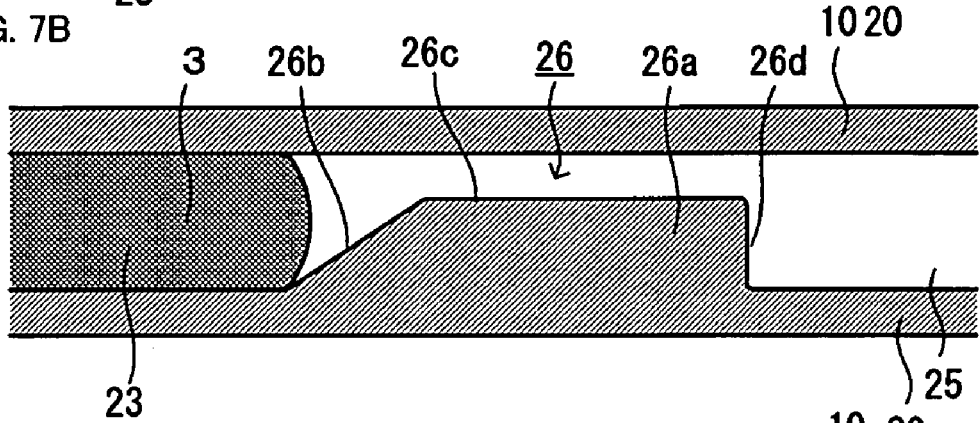

FIG. 7B shows a state in which the blood 3 has been sucked into the suction cavity 23. The blood 3 sucked by capillary phenomenon gets to the first portion 26b or to a part of the second portion 26c, but it will not go into any further and it is retained there.

Figure 7C:
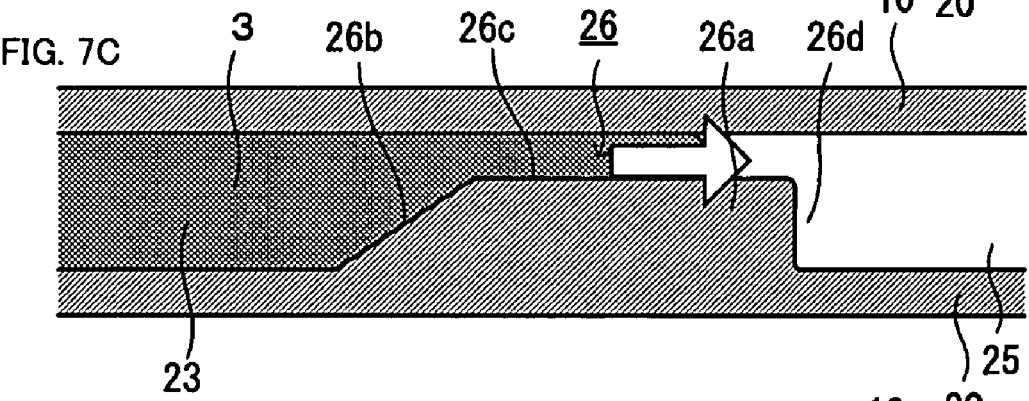
Figure 7D:
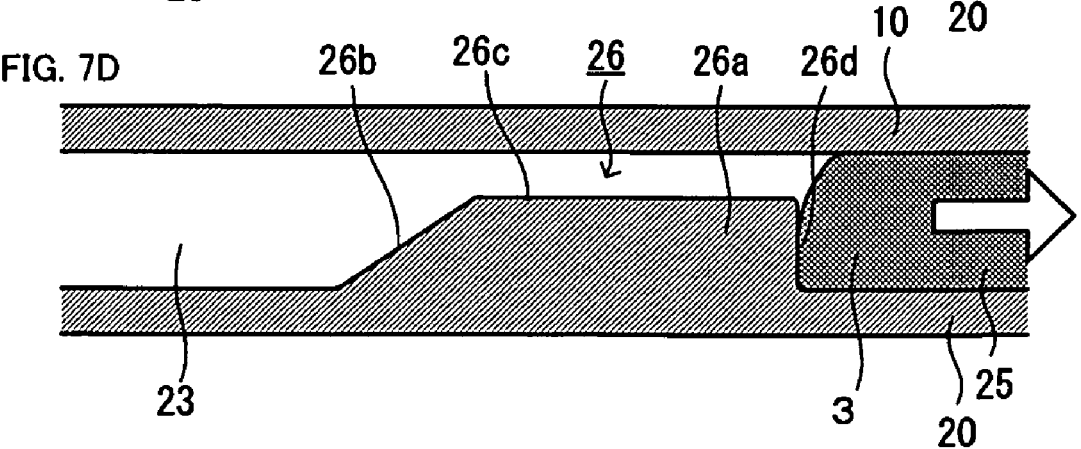

FIG. 7C and FIG. 7D show the status where a centrifugal force has been applied. The blood 3 which is applied the centrifugal force passes through the narrow gap at the second portion 26c of the narrowed section 26 (FIG. 7C), and then flows into the flow channel 25 from the third portion 26d of the narrowed section 26. Backward flow of the blood 3 towards the suction cavity 23 side, the blood having already flowed into the flow channel 25, is restricted by the third portion 26d of the narrowed section 26.

The configuration as shown in FIG. 6, and FIGS. 7A to 7D, includes the wall part 26a in the narrowed section 26, and the wall part is placed on the lower plate 20 side. However, it is also possible to configure the wall part 26a in the narrowed section 26 to be placed on the electrode substrate 10 side (on the plate-like member on the upper side). FIG. 8A to FIG. 8D show a configuration example in which the wall part of the narrowed section is provided on the electrode substrate side.

The narrowed section 26 as shown in FIGS. 8A to 8D has a structure that the wall part 26a projects from the electrode substrate 10, thereby narrowing the gap space between the electrode substrate 10 and the lower plate 20. Similar to the configuration as shown in FIG. 6, and FIGS. 7A to 7D, the wall part 26a includes the first portion 26b, the second portion 26c, and the third portion 26d. The first portion 26b forms a gentle slope, and a flat surface is formed at the second portion 26c for a predetermined distance, and at the third portion 26d, the second portion 26c is changed to the surface of the flow channel 25 (see FIG. 8A).

Figure 8A:
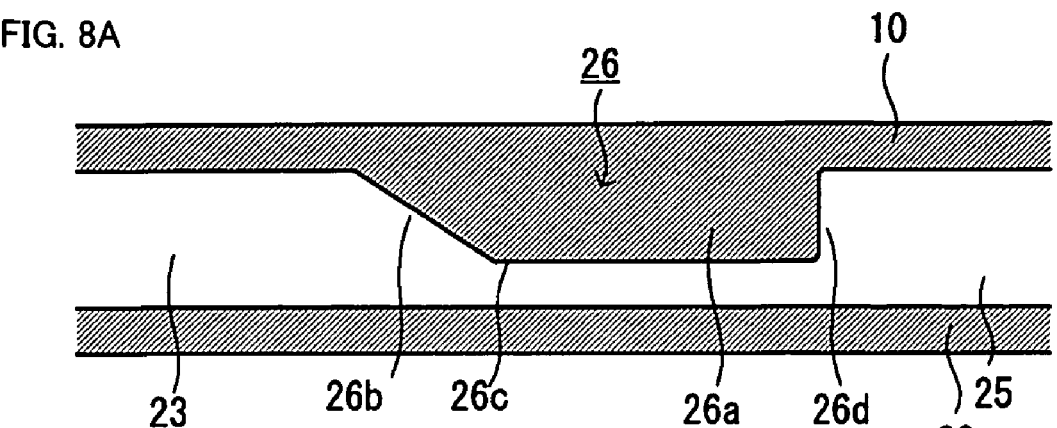
FIG. 8A, FIG. 8B, FIG. 8C, and FIG. 8D are cross sectional views showing the narrowed section provided in the biosensor according to the present invention.
Figure 8B:
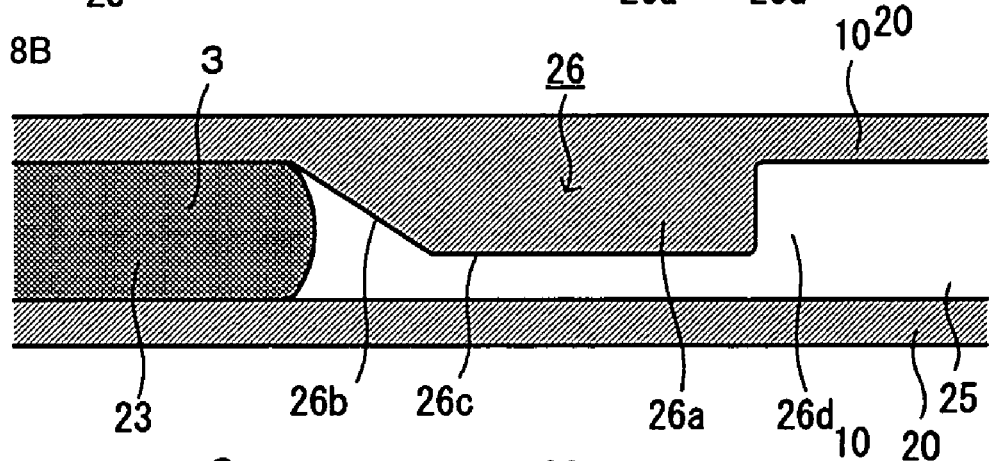
Figure 9:
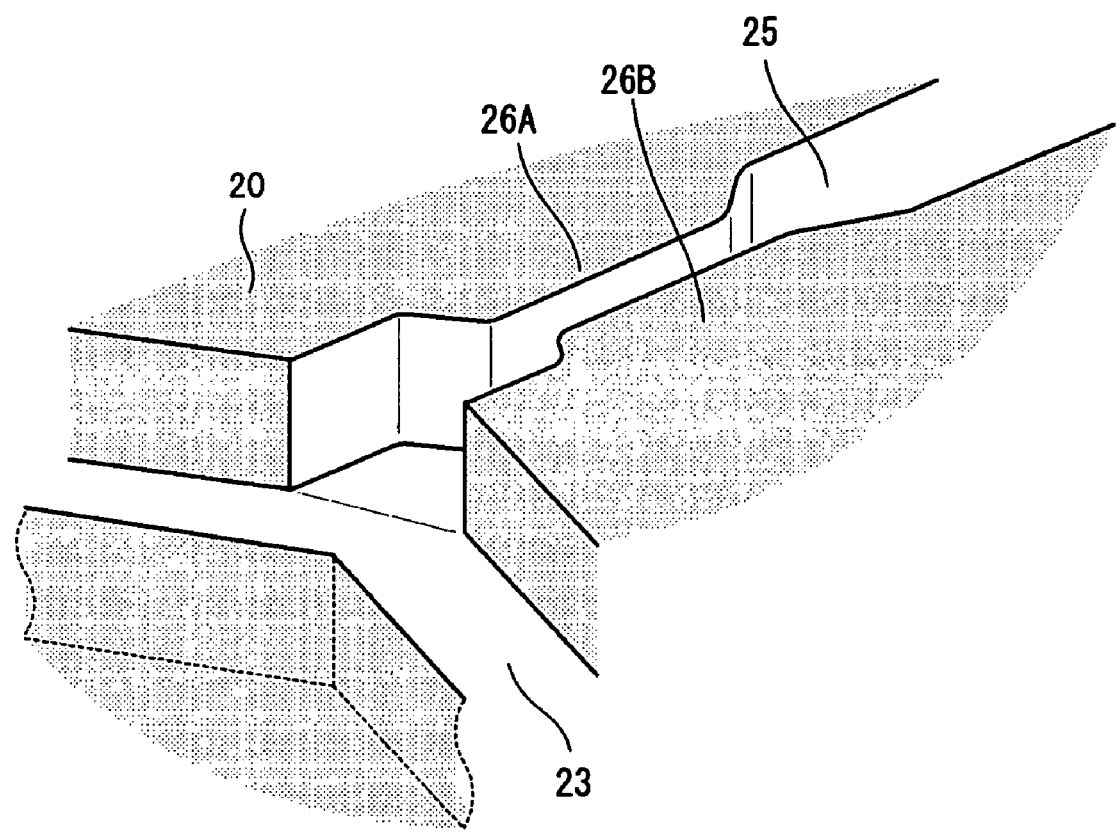
FIG. 9 is a perspective view showing the narrowed section provided in the biosensor according to the present invention.

FIG. 8B shows a state in which the blood 3 has been sucked into the suction cavity 23. The blood 3 sucked by capillary phenomenon gets to the first portion 26*b* or to a part of the second portion 26*c* of the narrowed section 26, but it will not go into any further and retained there.

Figure 8C:
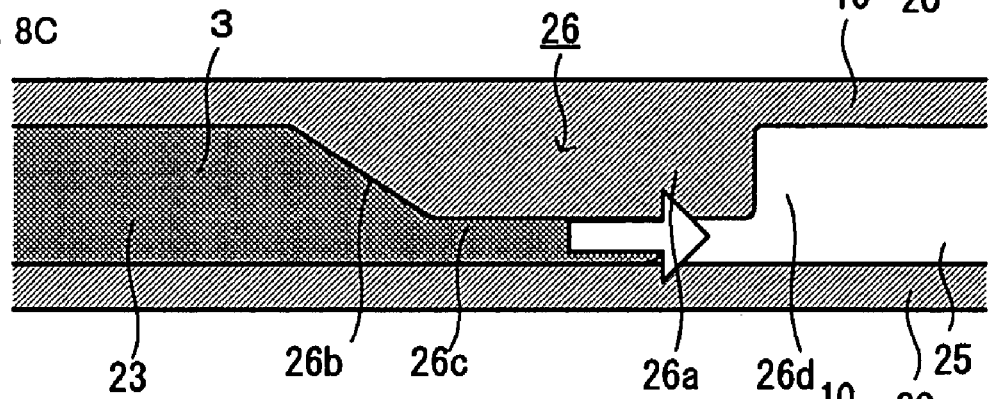
Figure 8D:
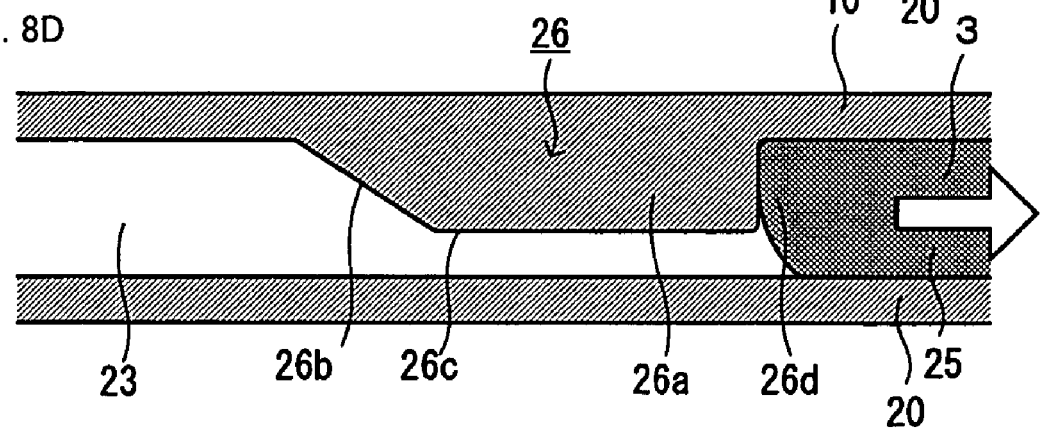

FIG. 8C and FIG. 8D show the state where a centrifugal force is applied. The blood 3 which is applied the centrifugal force passes through the narrow gap at the second portion 26*c* of the narrowed section 26 (FIG. 8C), and then flows into the flow channel 25 from the third portion 26*d* of the narrowed section 26. Backward flow of the blood 3 towards the suction cavity 23 side, the blood having already flowed into the flow channel 25, is restricted by the third portion 26*d* of the narrowed section 26.

The configuration as shown in FIG. 6 to FIG. 8D forms the narrowed section by the wall part provided either on the lower plate or on the electrode substrate, but the wall part may be provided both of the lower plate and the electrode substrate. In this case, it is possible to configure such that the wall parts are provided on the lower plate and the electrode substrate respectively on the positions opposed to each other. Alternatively, it is also possible to configure such that the wall parts are provided being displaced from each other in the flowing direction of the flow channel 25.

In addition, the configuration of the narrowed section 26 is not limited to the aforementioned one in which the wall part is provided in such a manner as projecting from the lower plate and/or the electrode substrate, towards the opposing electrode substrate and/or lower plate, respectively. Instead, it may be configured such that the wall part is provided on a sidewall of the lower plate or the electrode substrate. FIG. 9 shows a configuration example of the narrowed section in which the wall part is provided on the sidewall of the lower plate.

Wall parts 26A, 26B are formed by projecting the respective sidewalls of the lower plate 20 at one part of the flow channel 25, and a gap is formed by the portion between the wall parts 26A and 26B. Also in this configuration, as is the case of the aforementioned structure, each of the wall parts 26A and 26B includes the first to the third portions. That is, the first portion forms a gentle slope, a flat surface is formed at the second portion for a predetermined distance, and at the third portion, the second portion is changed to the surface of the flow channel 25.

Next, another embodiment of the biosensor according to the present invention will be explained.

Figure 10A:
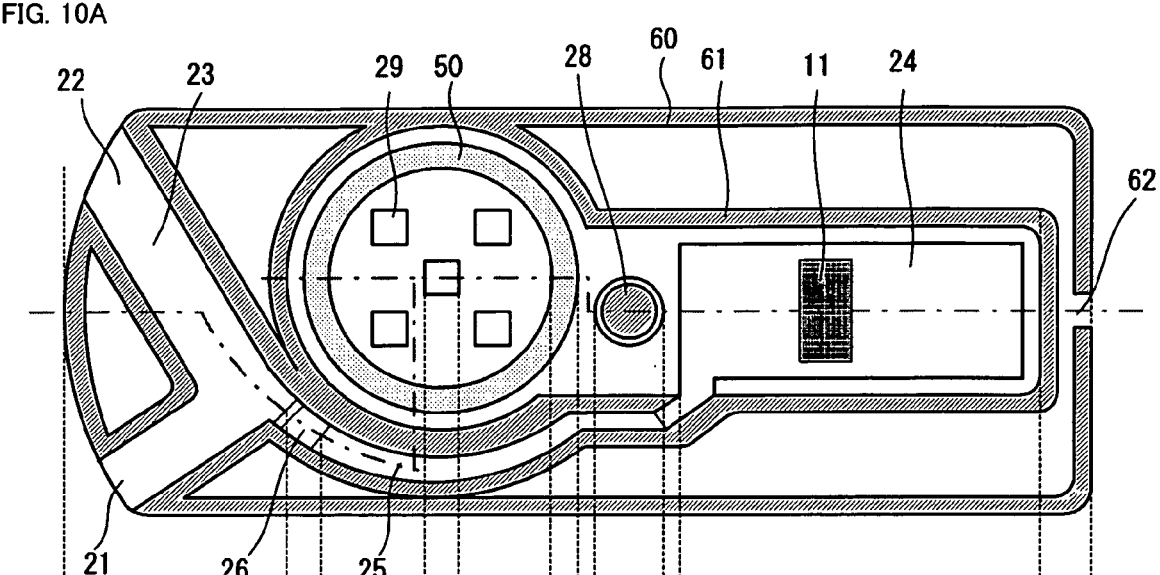
FIG. 10A is a plan view and FIG. 10B is a cross sectional view of a lower plate of the biosensor according to the second embodiment of the present invention.
Figure 10B:
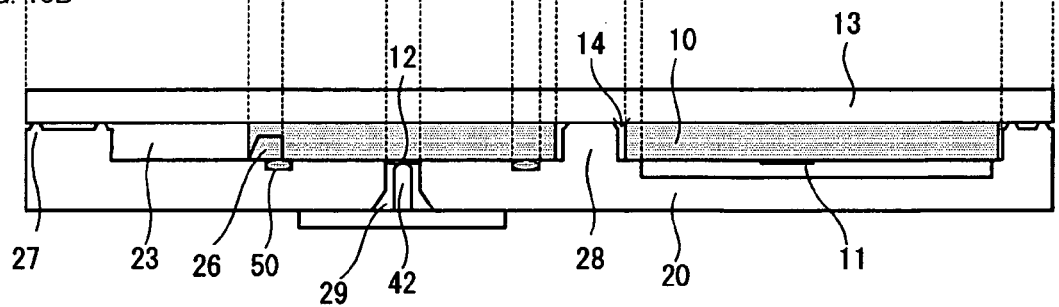

FIGS. 10A, 10B, FIG. 11, FIGS. 13A, 13B are explanatory views showing the biosensor according to the second embodiment of the present invention, and FIG. 10A is a plan view of the lower plate and FIG. 10B is a cross sectional view thereof. Since the configuration of the second embodiment is almost the same as the aforementioned first embodiment, the different elements are mainly explained here, and tedious explanation will not be given as to the common parts.

In FIGS. 10A, 10B, FIG. 11, FIGS. 13A, 13B, the biosensor 1 according to the second embodiment has a structure that the electrode substrate 10 is bonded between the upper plate 13 and the lower plate 20. This second embodiment shows an example in which concave portions are provided on the lower plate 20 side, thereby forming the suction cavity 23, analytical cavity 24, and the flow channel 25, and then, the upper plate 13 is arranged on the lower plate 20, placing the electrode substrate 10 therebetween, and they are bonded together by ultrasonic welding.

Figure 11:
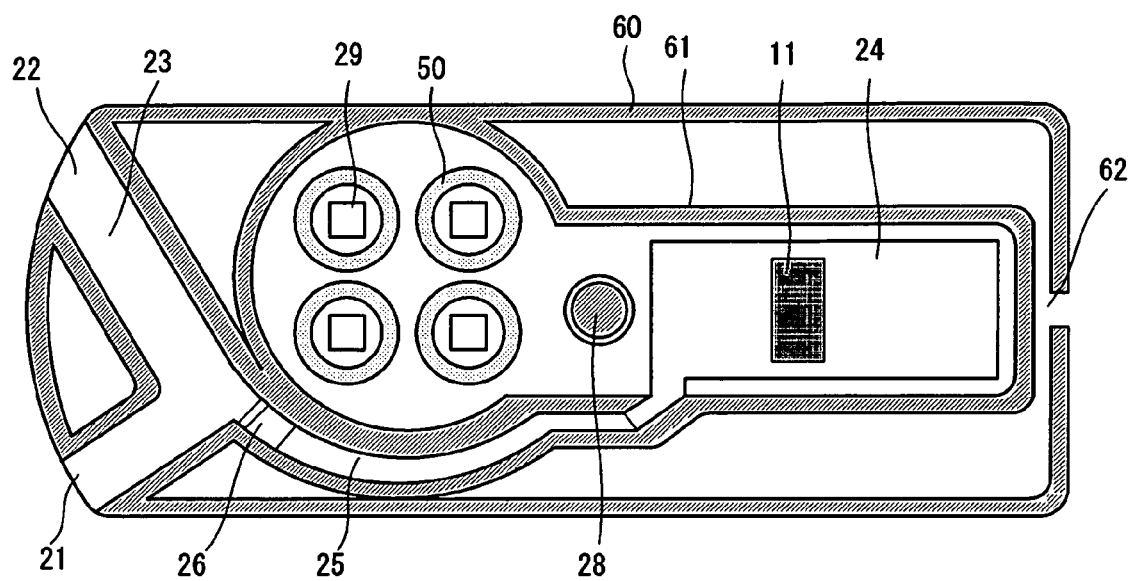
FIG. 11 is an explanatory view to explain the biosensor according to the second embodiment of the present invention.

In FIG. 10A and FIG. 11, the shaded portion indicates a position where the lower plate 20 and the upper plate 13 are bonded by the ultrasonic welding. The ultrasonic weld part 27 is formed so that it surrounds areas such as the suction cavity 23, analytical cavity 24, and the flow channel 25, which retain the sample inside. Furthermore, in FIGS. 10A, 10B, the lower plate 20 and the upper plate 13 are bonded by the ultrasonic welding also at the inner periphery portion 61 and outer periphery portion 60 of the biosensor.

It is further possible to form an opening 62 on a part of the outer periphery portion 60, as shown in FIGS. 10A, 10B, and FIG. 11. This opening 62 communicates the space between the inner periphery portion 61 and the outer periphery potion 60 of the biosensor, with the outside thereof, thereby preventing a damage against the ultrasonic weld portion when the gas within this space is expanded.

In addition to the ultrasonic weld part as described above, the part indicated by reference numeral 28 in FIGS. 10A, 10B, and FIG. 11 may be used for the ultrasonic welding. This weld part 28 is not only used for alignment for the upper plate 13, the electrode substrate 10, and the lower plate 20, but also used for pressing and fixing spacing-apart between the upper plate 13 and the lower plate 20, caused by elasticity of a leak prevention part such as an O-ring and a packing member, which will be described below. There is formed an opening 14 on the electrode substrate 10, so as to allow the weld part 28 of the lower plate 20 to pass through.

On one of the surfaces of the electrode substrate 10, there are formed an electrode 11 as described above, a connector terminal 12 to derive measured current generated on the electrode 11 to the outside, and this electrode 11 and the connector terminal 12 are connected by wiring. The connector terminal 12 is connected to an external analyzer by establishing connection with an external terminal such as a spring connector 42. On the lower plate 20, there is formed a connector window 29 at the position associated with the connector terminal 12. The external terminal is allowed to be electrically connected with the connector terminal 12 via this connector window 29.

Since the connector terminal 12 is connected with the electrode 11 via wiring, and the electrode 11 is arranged within the analytical cavity 24, the sample introduced in the analytical cavity 24 has a possibility to penetrate to the connector terminal 12 through the bonded surfaces between the lower plate and the electrode substrate and/or through the wiring, by way of capillary phenomenon or the like. Therefore, there is a possibility that a failure such as short-circuit occurs at the connector terminal 12.

Considering the above situation, the biosensor 1 is configured so that a failure due to short-circuit at the connector terminal 12 is prevented, and the position of the connecter terminal 12 is at least closer to the center of a centrifugal force rather than the analytical cavity 24, in the direction along which the centrifugal force is applied. In the configuration as shown in FIGS. 10A, 10B, and FIG. 11, the suction cavity 23 is positioned on the side closer to the center of the centrifugal force so that the blood in the suction cavity 23 is not let out when the centrifugal force is applied, and the analytical cavity 24 is arranged on the side away from the center of the centrifugal force. Here, the connector terminal 12 is arranged closer to the center of the centrifugal force, which is at least closer than the analytical cavity 24. When the centrifugal force is applied, this force acts to move the sample blood in the analytical cavity 24 away from the connector terminal 12. Accordingly, the sample blood in the analytical cavity 24 is prevented from arriving at the connector terminal 12.

In addition, the biosensor 1 according to the present invention has a configuration being provided with a seal of leak prevention part 50 such as O-ring and packing member, which surrounds the connector terminal 12 to prevent a short-circuit failure at the connector terminal 12. FIG. 10A and FIG. 10B show a configuration example of the leak prevention part 50 which surrounds multiple connector terminals 12 as a whole, and FIG. 11 shows a configuration example in which each of the multiple connector terminals 12 is surrounded independently. Further in the configuration surrounding the multiple connectors as a whole, it is also possible for one leak prevention part to surround arbitrary number of connectors, based on the arrangement of connectors and the like. This leak prevention part 50 prevents the sample blood, which is penetrating from the analytical cavity 24 via the bonded surfaces between the lower plate and the electrode substrate and/or wiring, from arriving at the connector terminal 12.

Figure 12A:
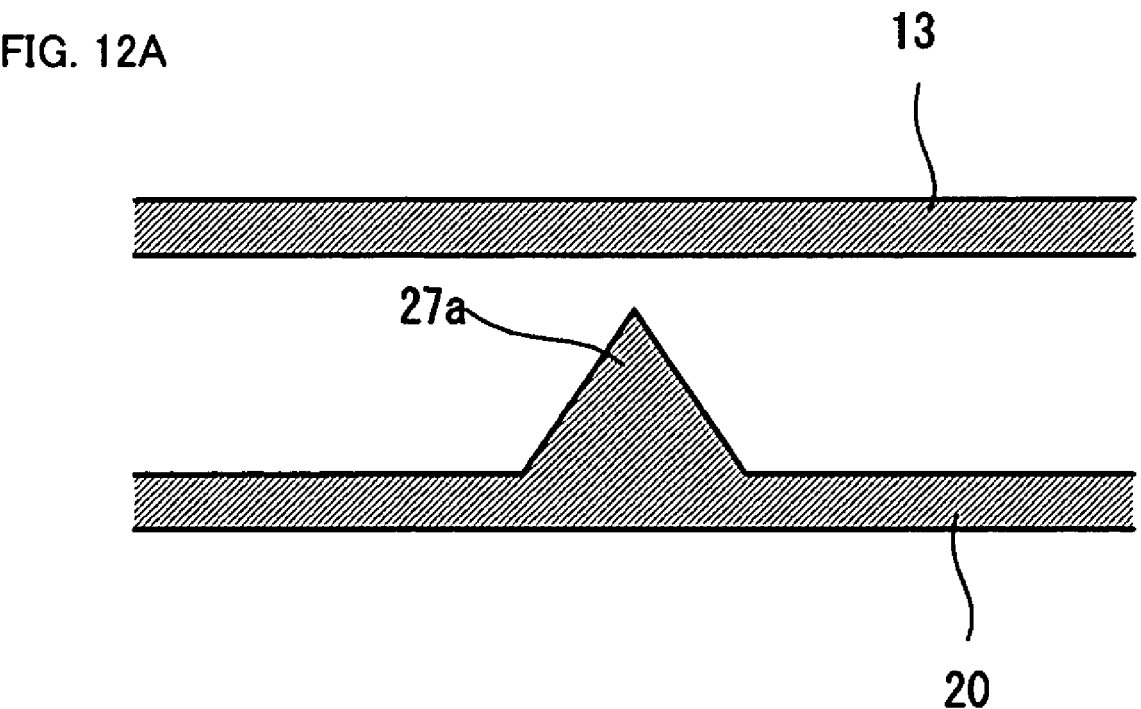
FIG. 12A and FIG. 12B are schematic cross sectional views to explain bonding of upper and lower plates by ultrasonic welding.
Figure 12B:
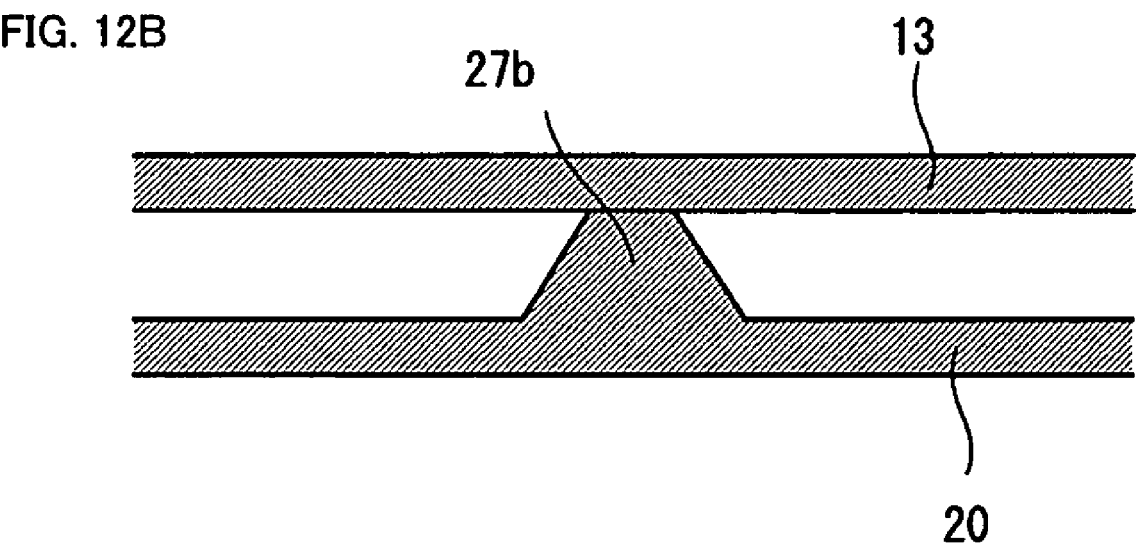

FIG. 12A and FIG. 12B are schematic cross sectional views to explain bonding between the upper plate and the lower plate by means of ultrasonic welding. FIG. 12A shows a state prior to the ultrasonic welding, and FIG. 12B shows a state after the ultrasonic welding is performed.

In FIG. 12A, the lower plate 20 made of synthetic resin is provided with a protruding portion 27a which projects towards the upper plate 13 at the position on which the ultrasonic welding is performed. When the upper plate 13 is made to approach the lower plate 20, the upper plate 13 abuts against the protruding portion 27a of the lower plate 20. In thus abutted status, an ultrasonic wave is emitted while a pressure is applied, then the protruding portion 27a is deformed as shown in FIG. 12B, and welded to the upper plate 13. When the protruding portion 27b is deformed, the volume of the space part between the upper plate 13 and the lower plate 20 is decreased. If this space part is being enclosed, there is a possibility that the inner pressure in the space part is increased, and this may cause a deformation or dissociation at the weld part. However, as described above, there is provided an opening 62 on the outer periphery of the biosensor, thereby preventing such deformation or dissociation of the weld part.

Figure 13A:
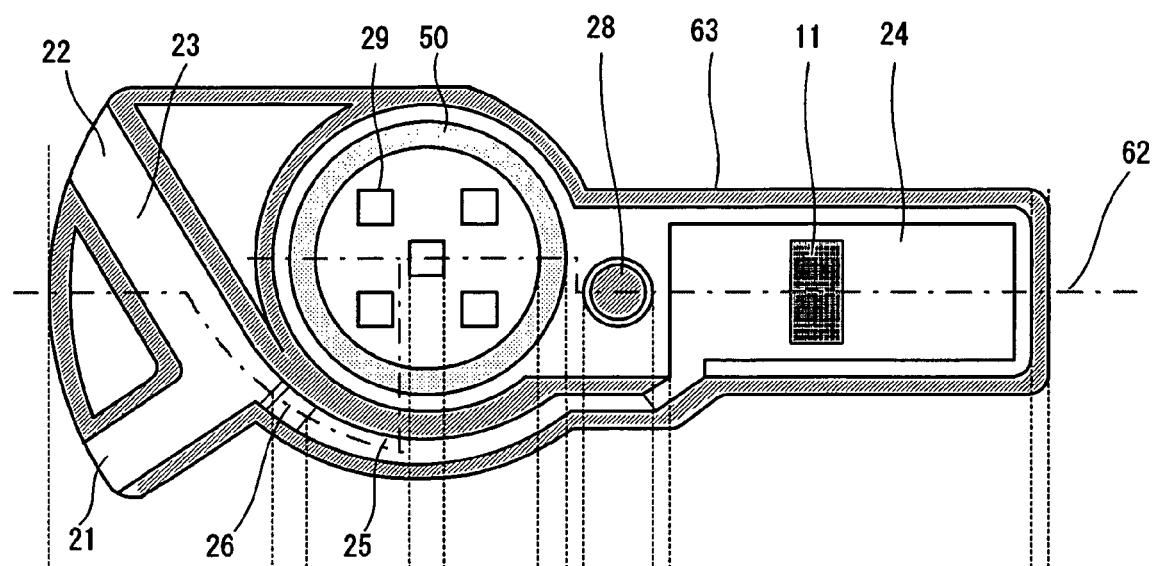
FIG. 13A and FIG. 13B are explanatory views to explain the biosensor according to the third embodiment of the present invention.
Figure 13B:
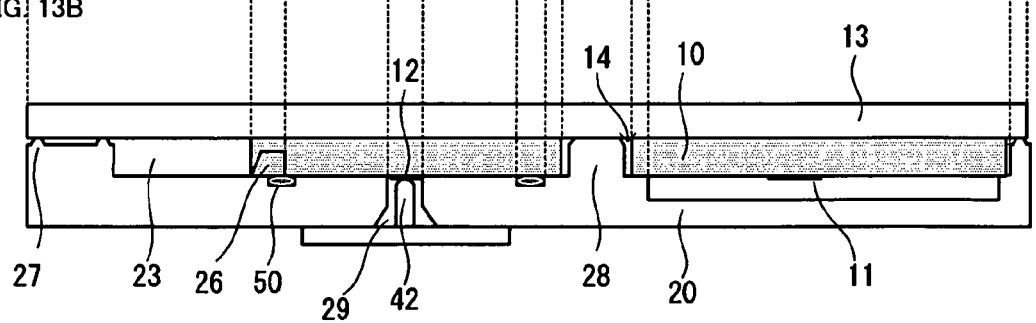

The configuration example as shown in FIG. 13A and FIG. 13B is the same as shown in FIG. 11, except that the configuration of FIGS. 13A and 13B do not include the outer periphery portion 60. In this example, the outer periphery portion 63 which forms the analytical cavity 24 is defined as the outermost periphery portion.

Next, the third embodiment of the biosensor according to the present invention will be explained with reference to FIG. 14A to FIG. 17C. In the third embodiment, the electrode is arranged on a surface of the electrode substrate, the surface being opposed to the analytical cavity 24, and a connector is placed on the other surface of the electrode substrate. With this layout above, connection is established between the connector and the external device by way of the connector window that is provided on the upper plate 13.

In the configuration example as shown in FIG. 14A to FIG. 14C, an electrode 11 is provided on one surface of the electrode substrate 10, and a connector terminals 12 is provided on the other surface side, and this point is different from each configuration as described in FIG. 11 and FIGS. 13A, 13B. Electrical connection is established between the electrode 11 and the connector terminal 12, via the wiring provided within the electrode substrate 10. The upper plate 13 is provided with the connector window 15 on the position which is associated with the connector terminal 12. The spring connector 42 being connected to the external device comes into electrical contact with the connector terminal 12, through the connector window 15, and derives a measured current from the electrode 11.

It is also possible to provide on the upper plate 13, a leak prevention part 16 such as O-ring and packing member to surround the connector terminal 12, so that the sample blood from the suction cavity 23 and the analytical cavity 24 is prevented from penetrating into the connector terminal 12. FIG. 14A and FIG. 14B are plan views of the upper plate and the lower plate, respectively, FIG. 14C is a cross sectional view of the lower plate, taken along the alternate long and short dash line in FIG. 14B.

Figure 15A:
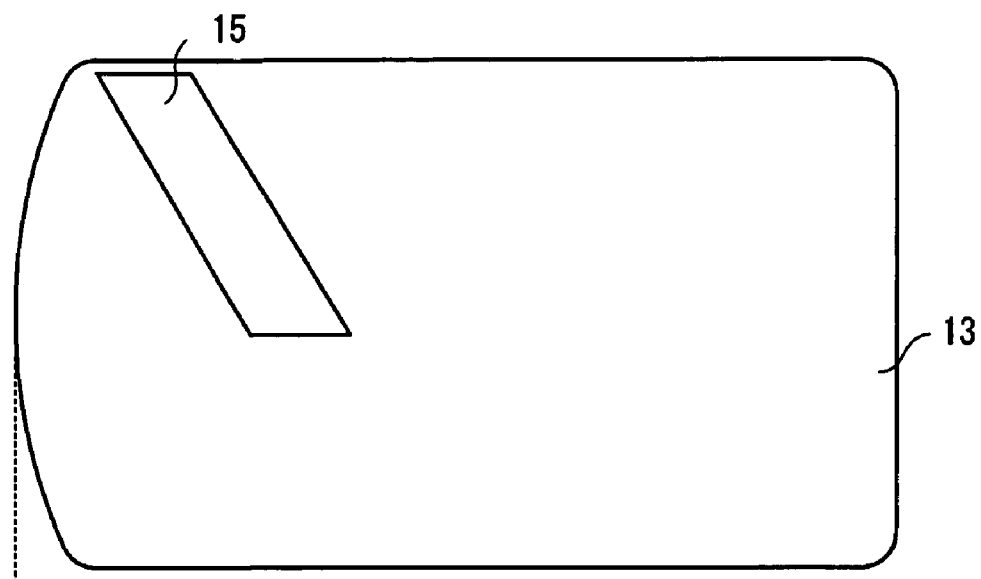
FIG. 15A, FIG. 15B, and FIG. 15C are explanatory views to explain the biosensor according to the third embodiment of the present invention.
Figure 15B:
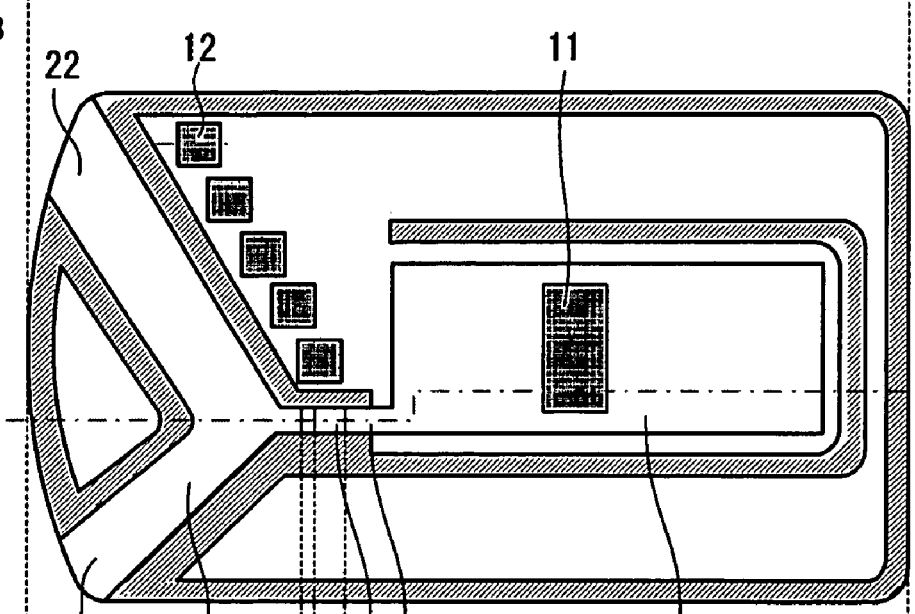
Figure 15C:
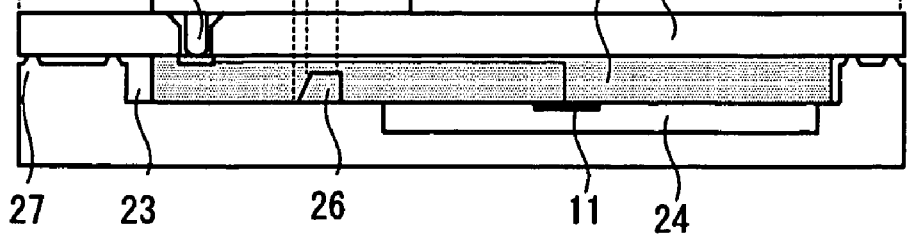

In the configuration example as shown in FIGS. 15A, 15B, and 15C, the electrode 11 is provided on one surface of the electrode substrate 10, and the connector terminal 12 is provided on the other surface side, similar to the configuration as shown in FIGS. 14A to 14C. There is provided a connector window 15 on the upper plate 13 at the position associated with the connector terminal 12, and the connector terminal 12 comes into electrical contact with the spring connector 42 via the connector window 15, and derives the measured current from the electrode 11.

In the configuration where the electrode 11 and the connector terminal 12 are provided respectively on opposite surfaces via the electrode substrate 10, it can be considered that transferring of the sample blood from the electrode 11 to the connector terminal 12 is small. Therefore, in the configuration example as shown in FIG. 15A to FIG. 15c, the leak prevention part such as O-ring and packing member, which are provided in the example of FIG. 14A to FIG. 14c, is omitted. FIG. 15A and FIG. 15B are plan views of the upper plate and the lower plate, respectively, and FIG. 15C is a cross sectional view of the lower plate, taken along the alternate long and short dash line in FIG. 15B.

Figure 16A:
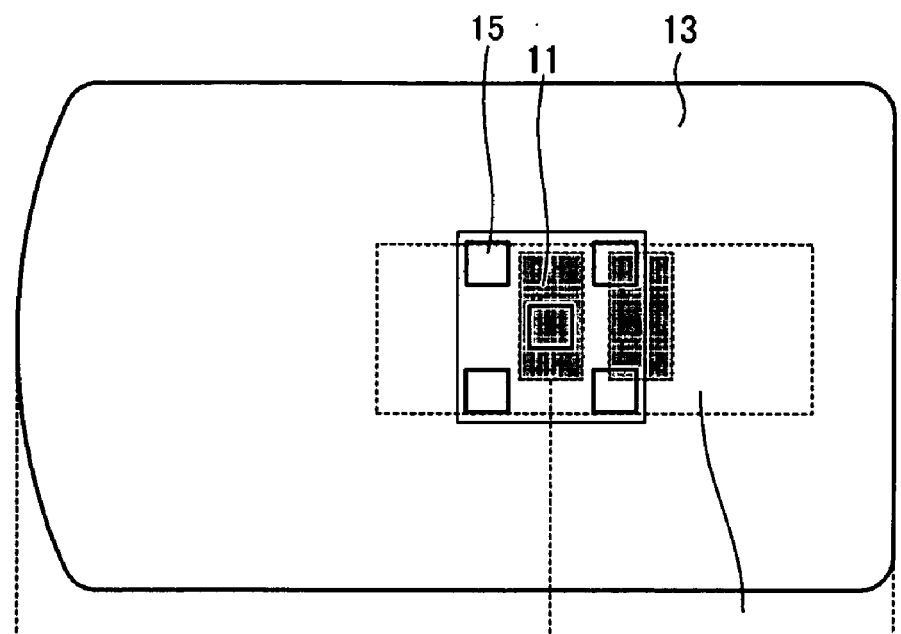
FIG. 16A, FIG. 16B, and FIG. 16C are explanatory views to explain the biosensor according to the third embodiment of the present invention.
Figure 16B:
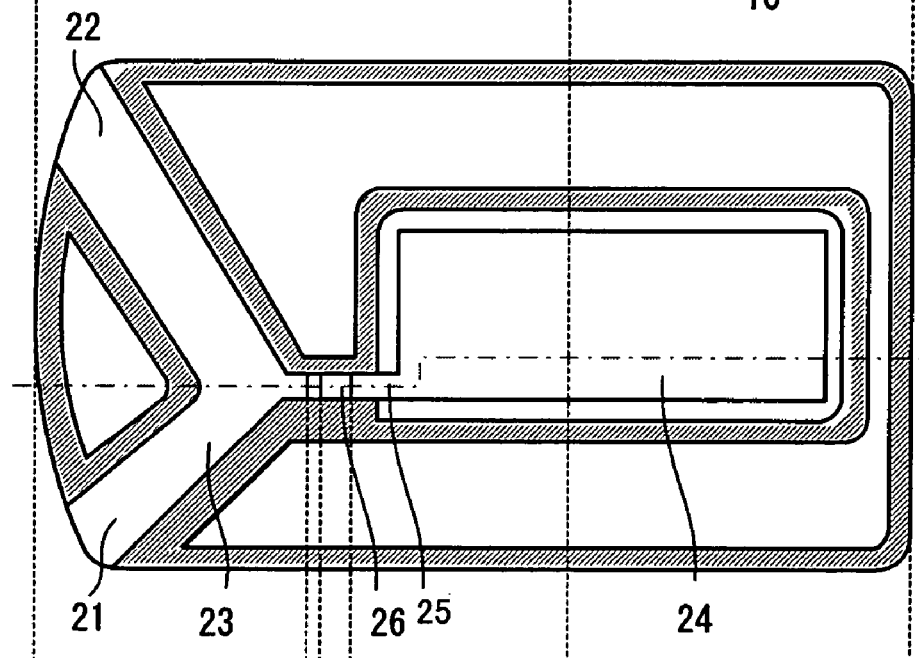
Figure 16C:
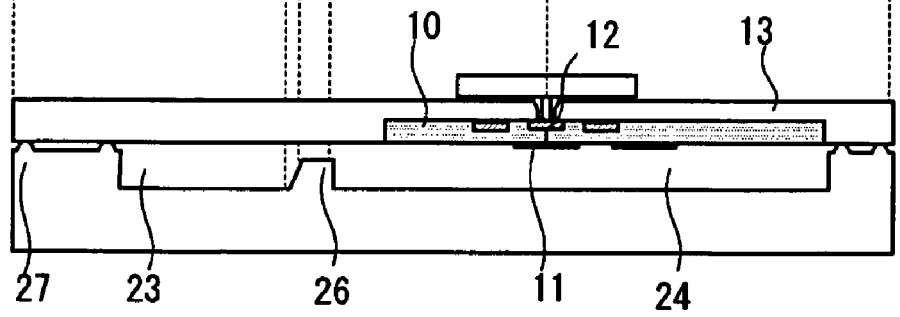
Figure 17A:
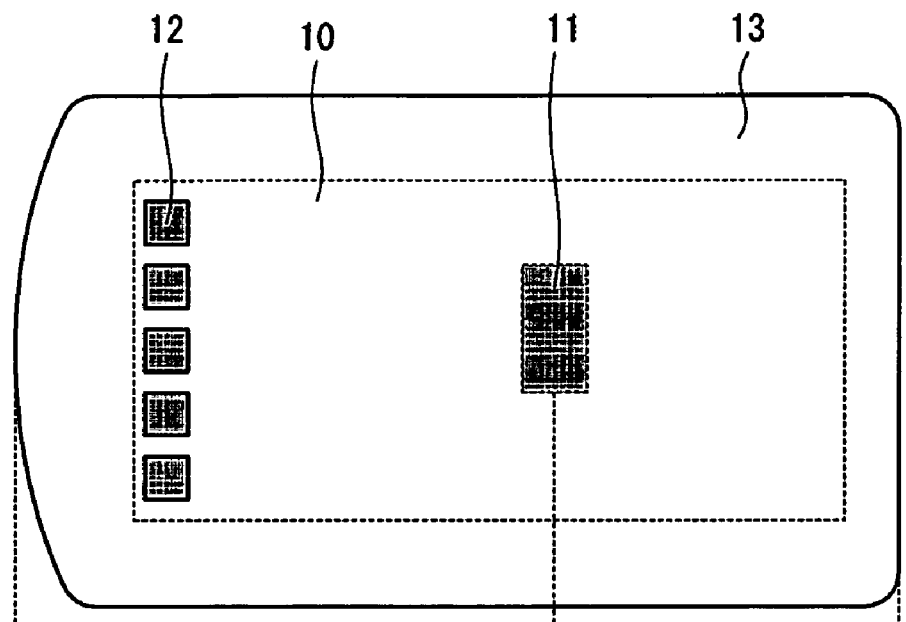
FIG. 17A, FIG. 17B, and FIG. 17C are explanatory views to explain the biosensor according to the third embodiment of the present invention.
Figure 17B:
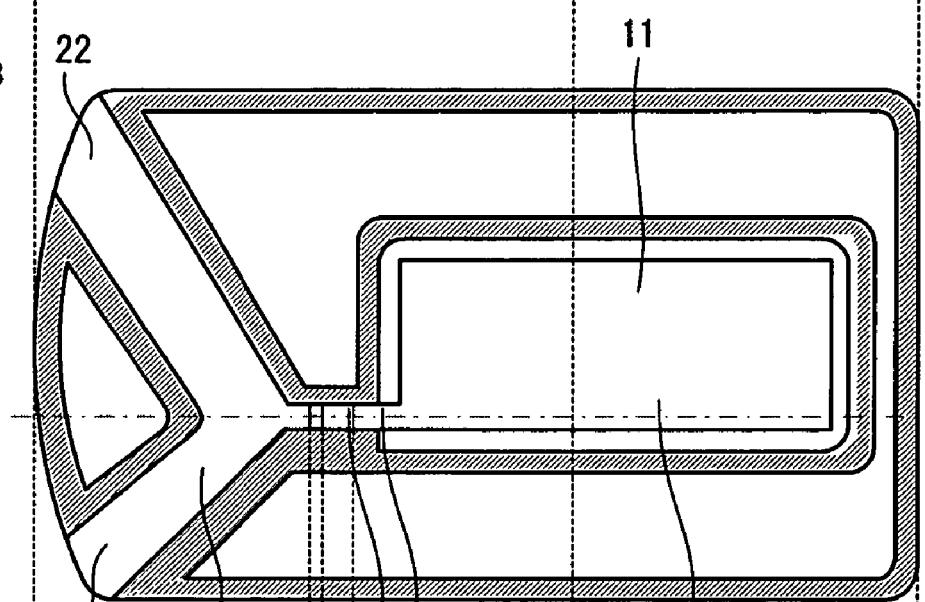
Figure 17C:
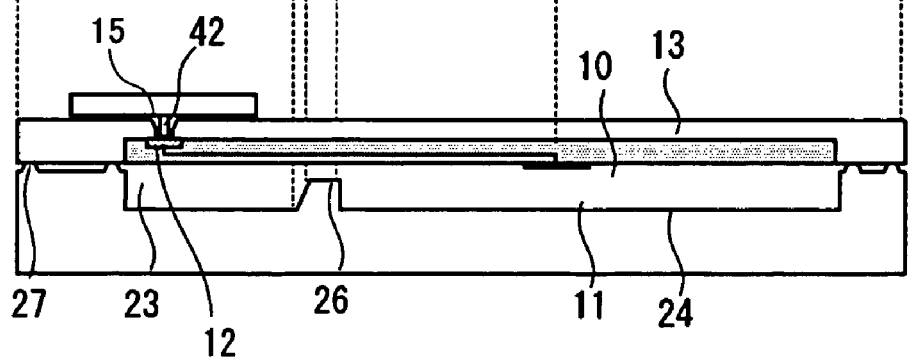

In the configuration as shown in FIGS. 16A, 16B, and 16C, and in FIGS. 17A, 17B, and 17C, similar to the configuration as shown in FIGS. 15A, 15B, and 15C, the electrode 11 is provided on one surface of the electrode substrate 10, and the connector terminal 12 is provided on the other surface, and further, on the upper plate 13, there is provided a connector window 15 at a position associated with the connector terminal 12. Through this connector window 15, the connector terminal 12 comes into electric contact with the spring connector 42, and derives the measured current from the electrode 11. Furthermore, in the configurations as shown in FIGS. 16A to 17C, the electrode substrate 10 is incorporated into the upper plate 13.

The configuration as shown in FIGS. 16A to 16C indicates an example where the connector window 15 is provided on the position opposed to the electrode 11, placing the electrode substrate 10 therebetween. The configuration as shown in FIGS. 17A to 17C indicates an example where the connector window 15 is provided on the position closer to the center of the centrifugal force rather than the electrode 11. FIGS. 16A, 16B, and FIGS. 17A, 17B are plan views of the upper plate and the lower plate, respectively, FIG. 16C and FIG. 17C are cross sectional views of the lower plate, taken along the alternate long and short dash line in FIG. 16B and FIG. 17B, respectively.

Figure 18A:
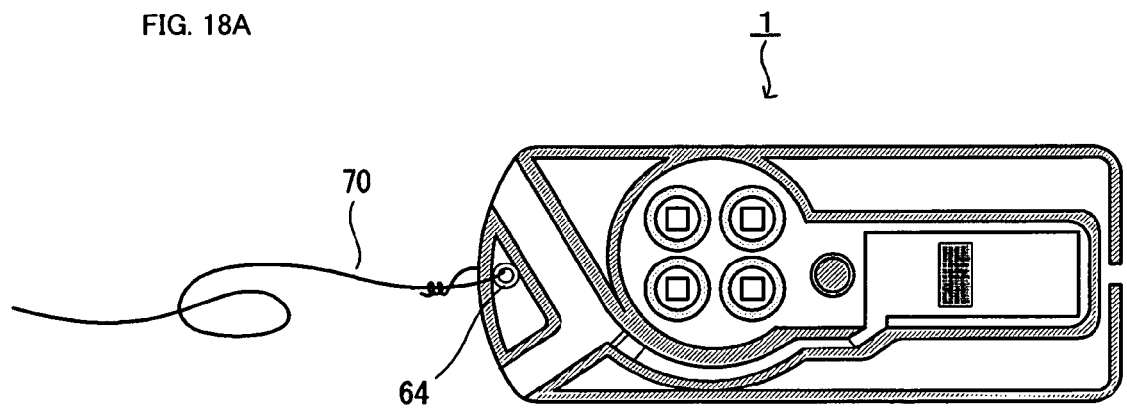
FIG. 18A and FIG. 18B are illustrations to explain manual application of centrifugal force to the biosensor.
Figure 18B:
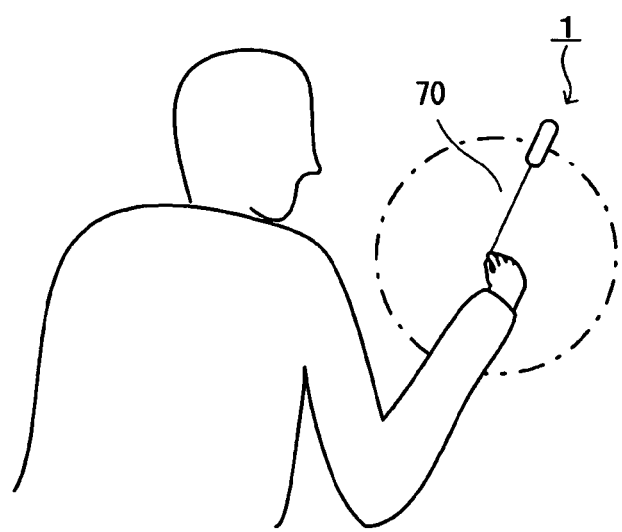

Application of the centrifugal force to the biosensor of the present invention can be performed by shaking the biosensor manually, instead of the configuration which drives the turntable as shown in FIG. 5 by a motor. FIG. 18A and FIG. 18B are explanatory views to explain the manual application of centrifugal force to the biosensor. In FIG. 18A, an opening 64 is provided on the edge of the biosensor 1 where the suction cavity 23 is formed, and one end of string 70 is tied to this opening 64.

By rotating the biosensor 1 while holding the other end of the string 70, the centrifugal force is applied to the biosensor 1. Alternatively, it is also possible that the edge of the biosensor 1 where the suction cavity 23 is formed is held by hand, and the centrifugal force is applied thereto by shaking the biosensor 1.

It is to be noted that if the centrifugal force is applied to the biosensor manually as described above, the force is smaller than the one applied by the motor drive. Therefore, it is anticipated that the sample blood may not be centrifugally separated by component, into the erythrocyte component 31 and the plasma component 32.

Therefore, this manual application of the centrifugal force on the biosensor enables a simple analysis, since it does not need a mechanism for motor drive, and it is applicable to an analysis which does not require any centrifugal separation.

What is claimed is:

1. A biosensor being provided with a suction cavity which sucks a certain amount of sample by means of capillary phenomenon, said biosensor comprising:
    a flow channel to connect said suction cavity and an analytical cavity furnished with a reagent, and
    a wall portion formed by projecting at least any one of an upper surface, a lower surface, and side walls of said flow channel, said wall portion provided on a part of said flow channel to form a narrowed section, said narrowed section is provided with a gap formed by narrowing a flow passage area due to said wall portion provided on said part of the flow channel,
    said sample is held back by the wall portion of said narrowed section so that said sample is retained in said suction cavity when the sample is sucked into said suction cavity, and allows the sample accumulated in said suction cavity to circulate into said analytical cavity through said gap, when a centrifugal force is applied from the outside, and
    said analytical cavity is not provided with an air vent, said analytical cavity vents air displaced by the sample from said suction cavity by way of the gap in the flow channel which communicates with an outlet for venting air provided in said suction cavity,
    wherein said narrowed section comprises:
    a first portion where a flow channel area is gradually decreased on the suction cavity side, and
    a second portion where the flow channel area stays narrow for a predetermined distance between said suction cavity side and said flow channel side, and wherein,
    said narrow area increases in the rear of said second portion, from said flow channel area having been narrowed to an original area of said flow channel.

2. The biosensor according to claim 1, wherein, said analytical cavity comprises an enzyme reaction layer for use in electrochemical measurement.

3. The biosensor according to claim 2, wherein, a plurality of said enzyme reaction layers are separately arranged along a direction to which the centrifugal force is applied, and said enzyme reaction layers are respectively associated with components of the sample being centrifugally separated.

4. The biosensor according to at least any one of claims 1 to 3, wherein, said suction cavity comprises:
    two openings placed in parallel, perpendicularly to the direction to which the centrifugal force is applied, and
    a joint which establishes connection with said flow channel, and,
    at said joint, a line from each of said two openings to said joint crosses the direction to which the centrifugal force is applied, in a positional relationship to form an obtuse angle, and the sample in said suction cavity receives a force directing to said flow channel by the centrifugal force.

5. The biosensor according to at least any one of claims 1 to 3, wherein,
    said suction cavity comprises a reagent for pretreating said sample.

6. The biosensor according to at least any one of claims 1 to 3, wherein, said suction cavity, flow channel, and analytical cavity are formed by bonding two plate-like members with surfaces opposed to each other, one or both of the surfaces having concave-convex parts.

7. The biosensor according to claim 6, wherein,
    an electrode substrate is placed between said two plate-like members, the electrode substrate having an electrode being exposed in said analytical cavity.

8. The biosensor according to claim 7, wherein,
    at least one of said plate-like members comprises a window part which electrically connects a connector intended for external connection with an external circuit, said connector being electrically connected with said electrode on the electrode substrate.

9. The biosensor according to claim 8, wherein,
    said plate-like member comprises either of an O-ring and a packaging member which surrounds said window part.

10. The biosensor according to claim 9, wherein,
    said plate-like member comprises either of an O-ring and a packaging member which surrounds a plurality of said window parts as a whole.

11. The biosensor according to claim 9, wherein, said plate-like member comprises either of a plurality of O-rings and a plurality of packaging members which respectively surround a plurality of said window parts individually.

12. The biosensor according to claim 8, wherein,
    said window part intended for the external connection is placed at a position closer to the center of the centrifugal force, which is at least closer than said analytical cavity, in the direction to which the centrifugal force is applied.

13. The biosensor according to at least any one of claims 1 to 3, wherein,
    ultrasonic welding is applied to an outer circumferential part of said suction cavity, flow channel, and analytical cavity.

14. The biosensor according to at least any one of claims 1 to 3, wherein,
    an outermost circumferential part of said plate-like member is subjected to the ultrasonic welding.

15. The biosensor according to at least any one of claims 1 to 3, wherein,
    hydrophilic coating is applied on a wall surface of said suction cavity.

16. The biosensor according to at least any one of claims 1 to 3, wherein,
    said hydrophilic coating is formed by applying surfactant.

17. The biosensor according to at least any one of claims 1 to 3, wherein,
    said narrowed section is hydrophobic.

18. The biosensor according to claim 17, wherein,
    said narrowed section is made of a hydrophobic synthetic resin.

19. The biosensor according to claim 17,
    a water-repellent treatment is applied on said narrowed section.

* * * * *